United States Patent
Min

(10) Patent No.: US 9,387,329 B2
(45) Date of Patent: Jul. 12, 2016

(54) SYSTEMS AND METHODS FOR DETERMINING VENTRICULAR PACING SITES FOR USE WITH MULTI-POLE LEADS

(75) Inventor: Xiaoyi Min, Thousand Oaks, CA (US)

(73) Assignee: PACESETTER, INC., Sylmar, CA (US)

( * ) Notice: Subject to any disclaimer, the term of this patent is extended or adjusted under 35 U.S.C. 154(b) by 1623 days.

(21) Appl. No.: 12/639,881

(22) Filed: Dec. 16, 2009

(65) Prior Publication Data

US 2011/0022112 A1   Jan. 27, 2011

Related U.S. Application Data

(63) Continuation-in-part of application No. 12/507,646, filed on Jul. 22, 2009, now Pat. No. 8,265,755.

(51) Int. Cl.
*A61N 1/00* (2006.01)
*A61N 1/362* (2006.01)
*A61N 1/368* (2006.01)

(52) U.S. Cl.
CPC ............. *A61N 1/3627* (2013.01); *A61N 1/3684* (2013.01)

(58) Field of Classification Search
CPC ..... A61N 1/3627; A61N 1/3684; A61N 1/362; A61N 1/3621; A61N 1/3622
USPC ................................................ 607/4, 9, 45, 14
See application file for complete search history.

(56) References Cited

U.S. PATENT DOCUMENTS

| 7,248,925 | B2 | 7/2007 | Bruhns et al. | |
| 2002/0177879 | A1* | 11/2002 | Ding et al. | 607/9 |
| 2005/0090870 | A1* | 4/2005 | Hine et al. | 607/17 |

* cited by examiner

*Primary Examiner* — Mallika D Fairchild

(57) ABSTRACT

Techniques are provided for use by implantable medical devices for controlling multi-site left ventricular (MSLV) pacing using a multi-pole left ventricular (LV) lead. In various examples, a reduced number of "V sense", "RV pace", and "LV pace" tests are performed to determine preferred or optimal interventricular pacing delays (VV) for use with MSLV pacing. Additionally, techniques are described for sorting the order by which LV sites are to be paced during MSLV pacing. Furthermore, techniques are described for detecting and addressing circumstances where AV/PV delays are longer than corresponding AR/PR delays during MSLV.

14 Claims, 14 Drawing Sheets

SYSTEMS AND METHODS FOR DETERMINING VENTRICULAR PACING SITES FOR USE WITH MULTI-POLE LEADS

CROSS-REFERENCE TO RELATED APPLICATIONS

This application is a continuation-in-part of copending U.S. patent application Ser. No. 12/507,646, of Min, filed Jul. 22, 2009, entitled "Systems and Methods for Optimizing Ventricular Pacing Delays for use with Multi-Pole Leads," which is incorporated by reference herein.

FIELD OF THE INVENTION

The invention generally relates to implantable cardiac stimulation devices such as pacemakers and implantable cardioverter-defibrillators (ICDs) and, in particular, to techniques for determining preferred or optimal multi-site interventricular (VV) pacing delays for use in pacing the ventricles using multi-pole left ventricular leads.

BACKGROUND OF THE INVENTION

Clinical studies related to cardiac pacing have shown that an optimal atrio-ventricular pacing delay (e.g., AV delay or PV delay) and/or an optimal interventricular pacing delay (e.g., VV delay) can improve cardiac performance. However, such optimal delays depend on a variety of factors that may vary over time. Thus, what is "optimal" may vary over time. An optimization of AV/PV pacing delay and/or VV pacing delay may be performed at implantation and sometimes, a re-optimization may be performed during a follow-up consultation. While such optimizations are beneficial, the benefits may not last due to changes in various factors related to device and/or cardiac function.

The following patents and patent applications set forth various systems and methods for allowing a pacemaker, implantable cardioverter-defibrillator (ICD) or other cardiac rhythm management (CRM) device to determine and/or adjust AV/PV/VV pacing delays so as to help maintain the pacing delays at optimal values: U.S. patent application Ser. No. 10/703,070, filed Nov. 5, 2003, entitled "Methods for Ventricular Pacing" now abandoned; U.S. patent application Ser. No. 10/974,123, filed Oct. 26, 2004, now abandoned; U.S. patent application Ser. No. 10/986,273, filed Nov. 10, 2004, now U.S. Pat. No. 7,590,446; U.S. patent application Ser. No. 10/980,140, filed Nov. 1, 2004, now abandoned; U.S. patent application Ser. No. 11/129,540, filed May 13, 2005; and U.S. patent application Ser. No. 11/952,743, filed Dec. 7, 2007. See, also, U.S. patent application Ser. No. 12/328,605, filed Dec. 4, 2008, entitled "Systems and Methods for Controlling Ventricular Pacing in Patients with Long Intra-Atrial Conduction Delays" and U.S. patent application Ser. No. 12/132,563, filed Jun. 3, 2008, entitled "Systems and Methods for determining Intra-Atrial Conduction Delays using Multi-Pole Left Ventricular Pacing/Sensing Leads". See, further, U.S. Pat. No. 7,248,925, to Bruhns et al., entitled "System and Method for Determining Optimal Atrioventricular Delay based on Intrinsic Conduction Delays." At least some of the techniques are implemented within the QuickOpt™ systems of St. Jude Medical.

In particular, techniques were set forth within at least some of these patent documents for exploiting various inter-atrial and interventricular conduction delays to determine preferred or optimal AV/PV/VV pacing delays. Techniques were also set forth for exploiting the VV delays to determine which ventricles should be paced—the left ventricle (LV), the right ventricle (RV), both ventricles, or neither, and in which order. In at least some examples, the implanted device (or an external programming device in communication with the implanted device) performs a series of tests to determine intrinsic AV/PV and VV conduction delays from which preferred pacing delays are determined. In particular, an "A sense" test is performed to detect intrinsic intra-atrial delays from which preferred AV/PV pacing delays are determined. A "V sense" test is performed to detect intrinsic ventricular events from which an intrinsic interventricular conduction delay ($\Delta$) is determined. An "RV pace" test and a separate "LV pace" test are performed to detect paced interventricular conduction delays (IVCD_RL and IVCD_LR, respectively) from which an intrinsic interventricular correction term ($\epsilon$) is determined. The optimal VV delay for use in biventricular pacing is then set based on $\Delta$ and $\epsilon$.

Issues can arise, though, when using a multi-pole LV lead for multi-site LV (MSLV) pacing. With a multi-pole LV lead—rather than having only a pair of tip and ring electrodes at a distal end of the lead—numerous electrodes are provided along the lead so that pacing/sensing can be performed at any of a variety of selected locations on or in the LV. With a multi-pole lead, the number of tests to be performed to optimize pacing delays can become numerous and time consuming. Typically, a separate V sense test would be employed for each of the LV electrodes (in combination with a particular RV electrode.) So, for example, for a quadra-pole LV lead, four V sense tests would be performed, one for each of the four electrodes of the LV lead. Likewise, typically, separate RV and LV pace tests would be employed for each of the LV electrodes (in combination with the RV electrode.) Again, for the example of a quadra-pole LV lead, four RV pace tests would be performed, one for each of the four electrodes of the LV lead. As such, the overall test time for optimizing VV pacing parameters for a multi-pole LV lead might be significant, with resulting costs and inconveniences to patient and clinician.

Accordingly, the invention is generally directed to providing improved test techniques for use with multi-pole leads to allow for more prompt and efficient determination of preferred or optimal VV pacing delays. Some aspects of the invention are directed to identifying the order by which a set of MSLV pacing pulses are to be delivered to various sites within the LV (i.e. to determine which LV site is to be paced first, which site is to be paced second, and so on.) Still other aspects are directed to addressing circumstances where the PV pacing delays to be used are longer than intrinsic PR delays or where the AV pacing delays to be used are longer than intrinsic AR delays.

SUMMARY OF THE INVENTION

In an exemplary embodiment, a method is provided for controlling the delivery of cardiac pacing therapy by an implantable cardiac rhythm management device equipped with a multi-pole ventricular lead having a plurality of electrodes. Briefly, preliminary multi-site interventricular pacing delays (VVT) are determined for the plurality of electrodes of the multi-pole lead based, at least in part, on multi-site interventricular conduction time delay values ($\Delta$) determined for the electrodes. Multi-site interelectrode pacing delays (IVV) are determined for the plurality of electrodes of the multi-pole lead based the preliminary interventricular pacing delays (VVT). The order by which the electrodes of the multi-pole lead are to be used to deliver a set of multi-site pacing pulses is then determined, with the order set based on the interelectrode pacing time delays (IVV). A set of multi-site pacing pulses is then delivered using the electrodes of the multi-pole lead in the sorted order.

In an illustrative example, the implantable device is a pacemaker, ICD or cardiac resynchronization therapy (CRT) device equipped with a multi-pole LV lead having a plurality of individual LV electrodes ($LV_n$). The device is also equipped with an RV lead having at least one RV electrode. The overall method is performed to control MSLV pacing delivered using some combination of RV and LV electrodes. In one particular example, the LV lead has four electrodes—a tip electrode and three ring electrodes arrange sequentially along the lead adjacent the LV. Herein, the four electrodes of the quadrapole example are denoted n=1, 2, . . . , N where N=4. That is, the first or tip electrode is denoted n=1. The first ring electrode is denoted n=2, and so on.

In a quadra-pole example, the multi-site interventricular pacing time delays are determined by determining a preliminary interventricular pacing delay ($VV_n$) for use with a selected electrode ($LV_n$) of the LV lead based on:

$$VVT_n = \alpha^*(\Delta'_n + \epsilon_n); \text{ wherein } n=1, 2, 3, 4$$

wherein $\alpha_n$ is 0.5 (or other suitable coefficient), $\Delta'_n$ is an intrinsic interelectrode conduction time delay obtained within the patient, and $\epsilon_n$ is an interventricular correction term for use with the selected electrode ($LV_n$) of the LV lead.

In the quadra-pole example, the interelectrode conduction time delay ($\Delta'_n$) can be determined using:

$$\Delta'_n = \Delta_n - \Delta_{n-1}; \text{ where } n=2, 3, \ldots, N$$

$$\Delta'_1 = \Delta_1$$

wherein $\Delta_n$ is a measured intrinsic interventricular conduction time delay for the nth electrode of the multi-pole lead, which is measured within the patient based on intrinsic depolarization events, such as during a V-sense test. In the quadrapole example, the interventricular correction term ($\epsilon_n$) is determined based on:

$$\epsilon_n = IVCD(L_n L_{n-1}) - IVCD(L_{n-1} L_n) \text{ where } n=2, 3, \ldots, N$$

$$\epsilon_1 = IVCD(L_1 R) - IVCD(R L_1)$$

wherein IVCD represents the paced interventricular conduction time delay (IVCD) for various pairs of electrodes of the system as determined using RV pace and LV pace tests and N is the number of electrodes.

In the quadra-pole example, the order by which LV sites are to be paced is determined by: selectively summing values of $VVT_n$ to generate values for the interelectrode pacing delays ($IVV_n$); determining absolute values of each of the $IVV_n$ values; identifying the $IVV_n$ value having the maximum absolute value and selecting the corresponding electrode (n) as being the first electrode to be paced; and then repeating the process with the remaining $IVV_n$ values and the remaining electrodes to iteratively sort the $IVV_n$ values and the corresponding electrodes.

In one particular quadra-pole embodiment, the device calculates the set of $IVV_n$ values using:
  Sum=0
  IVV(0)=0 (for RV electrode)
  For i=1 to 4
    Sum=Sum+VVT(i);
    IVV(i)=Sum;
  End loop.
The device then assesses the relative absolute values of the IVV values to sort the order the LV pacing sites. The device also determines final interventricular pacing delays ($VV_n$) for use with each of the electrodes of the LV lead based on differences between $IVV_n$ values of the electrodes. In an illustrative example, the order with which stimulation pulses are to be delivered to the four electrodes of the LV lead is determined to be: 3rd electrode, 1st electrode, 2nd electrode and 4th electrode, with the RV electrode paced last. That is, the sorted order is: IVV(3), IVV(1), IVV(2), IVV(4), RV=0. In that example, the VV delay applied at the 3rd electrode ($VV_3$) is IVV(3); the VV delay applied at the 1st electrode ($VV_1$) is IVV(3)-IVV(1); the VV delay applied at the 2nd electrode ($VV_2$) electrode is IVV(1)-IVV(2); the VV delay applied at the 4th electrode ($VV_4$) electrode is IVV(2)-IVV(4); and the delay applied to the RV electrode is IVV(4)-0.

Also, in the exemplary embodiment, steps are taken to address circumstances where PV pacing delays to be used are longer than intrinsic PR delays or where the AV pacing delays to be used are longer than intrinsic AR delays (i.e. where the PV/AV values are too long resulting in intrinsic ventricular depolarization before paced depolarization.) In one particular example, A sense and A pace tests are performed. In the A sense test, the device measures an intrinsic atrioventricular time delay ($PR_{RV}$) between a P-wave and an RV QRS and then determines an intrinsic atrioventricular time delay ($PR_{LVn}$) between the P-wave and each of the plurality of LV electrodes. In the A pace test, the device measures an atrioventricular time delay ($AR_{RV}$) between an initial A-pulse and an RV QRS and then determines a paced atrioventricular time delay ($AR_{LVn}$) between the initial A-pulse and each of the plurality of LV electrodes. The device determines whether the resulting PV values exceed corresponding PR value and if so, LV pacing is delivered using two or more other electrodes where PV does not exceed the corresponding PR. For example, LV pacing sites are identified where $PV+VV_n<PR(L_n)$ and then pacing is delivered at those sites without pacing the RV. Similar considerations apply to circumstances where AV exceeds the corresponding AR value.

Although described primarily with respect to implementations having a multi-pole LV electrode, aspects of the invention are also applicable, where appropriate, to multi-pole RV leads or multi-pole atrial leads as well. In general, techniques are provided herein to determine interchamber conduction delays (such as a paced interchamber conduction time delay and an intrinsic interchamber conduction time delay) for setting interchamber pacing delays and for determining the order at which stimulation is delivered among multi-sites within a given chamber. Note also that, herein, by "interventricular", it is meant that the delays are between different sites within the ventricles. Interventricular delays can broadly include, e.g., delays between LV sites and RV sites, as well as delays between different LV sites. Delays between different LV sites can also be referred to as LV "intraventricular" delays or LV "interelectrode" delays.

System and method implementations of various exemplary techniques are presented herein.

BRIEF DESCRIPTION OF THE DRAWINGS

Features and advantages of the described implementations can be more readily understood by reference to the following description taken in conjunction with the accompanying drawings.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Overview of Implantable System

Figure 1:
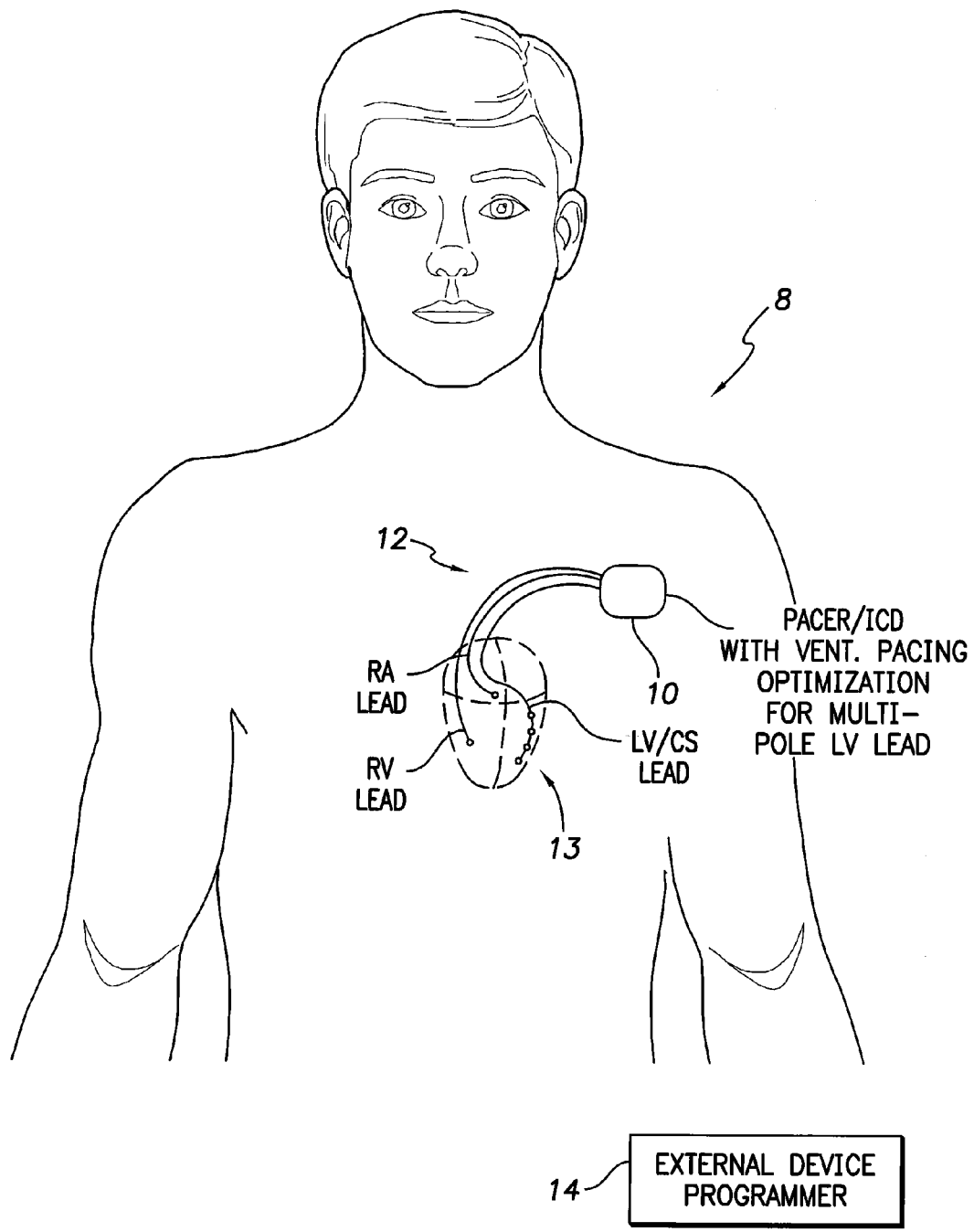
FIG. 1 illustrates pertinent components of an implantable medical system having a pacemaker or ICD capable of optimizing ventricular pacing delays for use with a multi-pole LV lead.

FIG. 1 illustrates an implantable medical system 8 capable of performing rapid optimization of ventricular pacing parameters using a multi-pole lead. The medical system 8 includes a pacer/ICD 10 or other cardiac rhythm management device equipped with one or more cardiac sensing/pacing leads 12 implanted on or within the heart of the patient, including a multi-pole LV lead implanted via the coronary sinus (CS). In FIG. 1, a stylized representation of the set of leads is provided. To illustrate the multi-pole configuration of the LV lead, a set of electrodes 13 is shown distributed along the LV lead. The RV and RA leads are each shown with a single electrode, though each of those leads may include additional electrodes as well, such as tip/ring electrode pairs. Still further, the LV lead can also include one or more left atrial (LA) electrodes mounted on or in the LA via the CS. See FIG. 8 for a more complete and accurate illustration of various exemplary leads.

In some implementations, the pacer/ICD itself performs the multi-pole optimization based on electrocardiac signals sensed using the leads. In other implementations, the device transmits features of the electrocardiac signals to an external device programmer 14 that performs the optimization. That is, the device programmer determines optimal multi-pole ventricular pacing parameters, which are then programmed into the pacer/ICD via telemetry. Other external devices might instead be used to perform the optimization, such as bedside monitors or the like. In some embodiments, the device programmer or bedside monitor is directly networked with a centralized computing system, such as the HouseCall™ system or the Merlin@home/Merlin.Net systems of St. Jude Medical.

In the following examples, it is assumed that the pacer/ICD performs the multi-pole optimization using on-board components. An example where the external programmer performs the optimization is described below with reference to FIG. 10. FIGS. 2-7 illustrate a first set of exemplary techniques for multi-pole optimization, also described in the aforementioned parent patent application. FIGS. 11-14 illustrate a second set of exemplary techniques wherein the order by which LV sites are to be paced are sorted and wherein circumstances are identified and addressed where PV/AV delays are longer than corresponding PR/AR delays.

Multi-Pole LV Pacing Optimization

Figure 2:
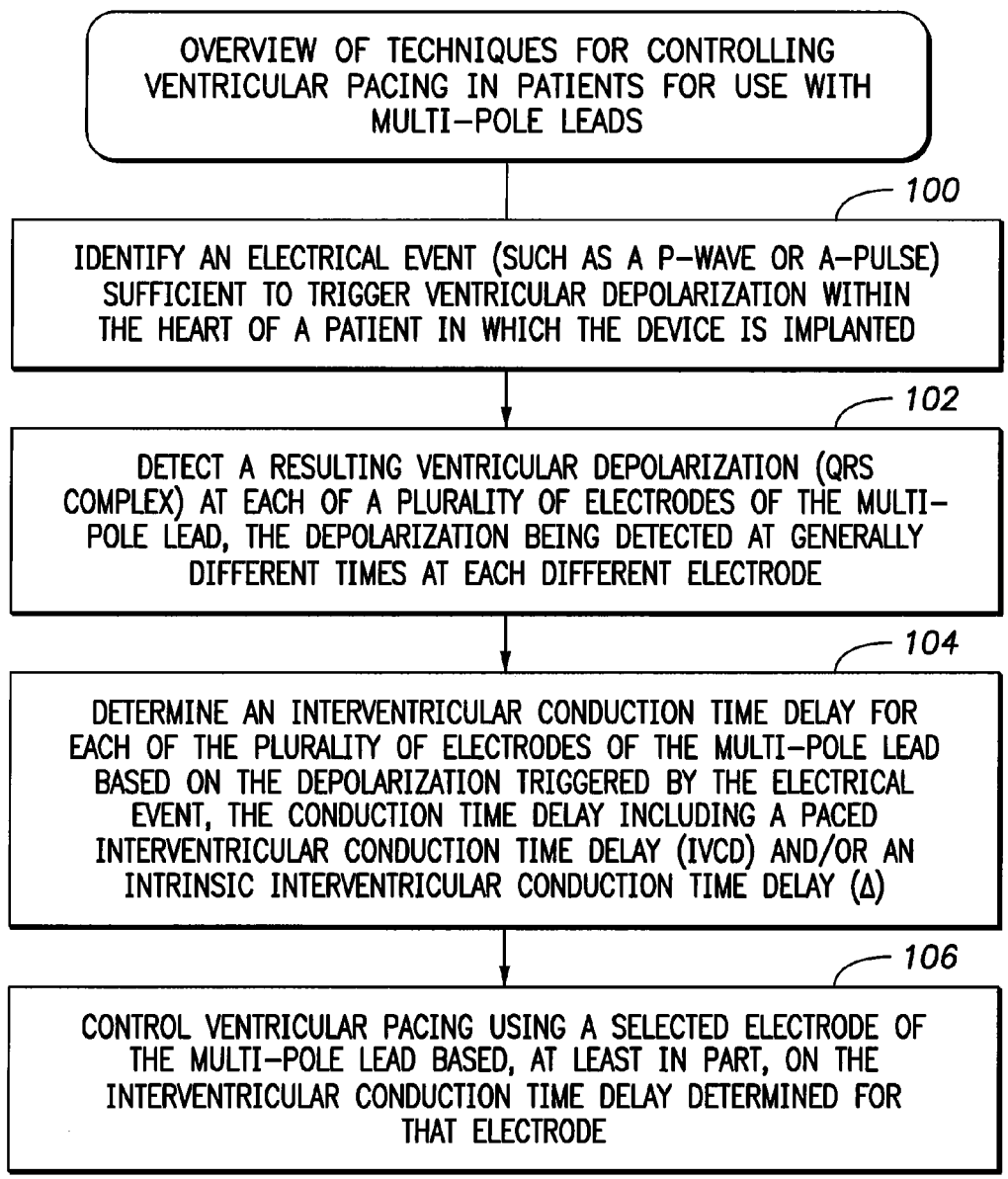
FIG. 2 is a flowchart providing an overview of a technique for controlling ventricular pacing using a multi-pole LV lead, which may be performed by the system of FIG. 1.

FIG. 2 broadly summarizes a general technique for controlling ventricular pacing parameters for use with a multi-pole ventricular lead that may be exploited by the pacer/ICD of FIG. 1 or other suitably equipped systems. Beginning at step 100, the pacer/ICD identifies an electrical event (such as a P-wave or an A-pulse) sufficient to trigger ventricular depolarization within the heart of the patient in which the device is implanted. At step 102, the pacer/ICD detects a resulting ventricular depolarization (QRS complex) at each of a plurality of electrodes of the multi-pole lead, the depolarization being detected at generally different times at each different electrode. In the examples described herein, the multi-pole lead is an LV lead, but it should be understood that the general techniques of the invention are applicable to multi-pole RV leads. Indeed, the techniques are applicable to implementations wherein both the LV and RV have multi-pole leads. Still further, the techniques are also generally applicable to multi-pole atrial leads, implanted on or in either the RA or the LA. As such, at least some of the techniques described herein are generally applicable to optimizing various interchamber pacing delays.

At step 104, the pacer/ICD determines an interventricular conduction time delay for each of the plurality of electrodes of the multi-pole lead based on the depolarization triggered by the electrical event. The conduction time delay is a paced interventricular conduction time delay (IVCD) and/or an intrinsic interventricular conduction time delay ($\Delta$). At step 106, VV pacing delays for use in controlling ventricular pacing using a selected electrode of the multi-pole lead can then be determined, at least in part, on the conduction time delay determined for the selected electrode. Alternatively, monoventricular pacing can be controlled by using the sign of VV from conduction time delay to determine the chamber to receive the monoventricular pacing pulses (i.e. RV vs. LV.)

Figure 3:
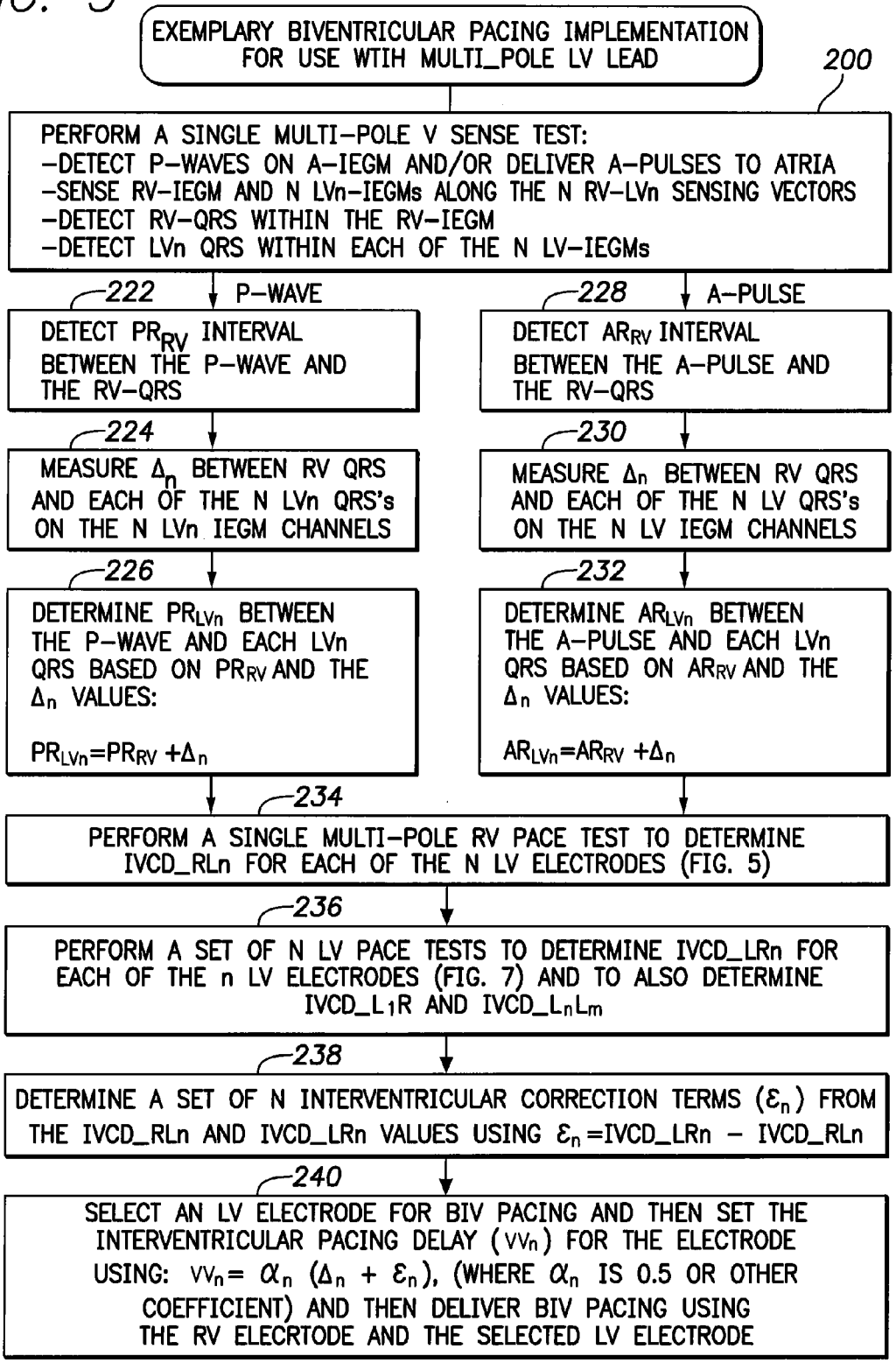
FIG. 3 is a flowchart illustrating an exemplary biventricular implementation of the technique of FIG. 2 wherein V sense, RV pace and LV pace tests are used to determine optimal biventricular pacing delays.

FIG. 3 provides a more detailed example wherein biventricular pacing is controlled for use with a multi-pole LV lead having N electrodes (individually denoted LVn). Beginning at step 200, the pacer/ICD performs a single V sense test. During the V sense test, the pacer/ICD: detects P-waves on an A-IEGM channel sensed using an RA lead and/or delivers A-pulse to the RA using the RA lead. The P-waves may be detected during a contemporaneous A sense test. The A-pulses may be delivered during a contemporaneous A pulse test. That is, the V sense test may be performed at the same time as A sense/A pace tests to enhance overall test efficiency. See the patent documents cited above for discussions of A sense/A pace tests, which are generally used to determine intra-atrial (AE/PE) delays for use in setting atrioventricular pacing delays (AV/PV).

Also at step 200, the pacer/ICD senses RV-IEGM and N individual LVn-IEGM signals along N sensing vectors between the RV tip electrode and each of the respective LVn electrodes. The device also detects LVn-QRS events within the LVn-IEGMs and detects RV-QRS events within the RV-IEGM. Exemplary RV and LVn IEGMs are shown in FIG. 4 (in stylized form) for a quadra-pole example wherein the LV lead has four pacing/sensing electrodes.

Figure 4:
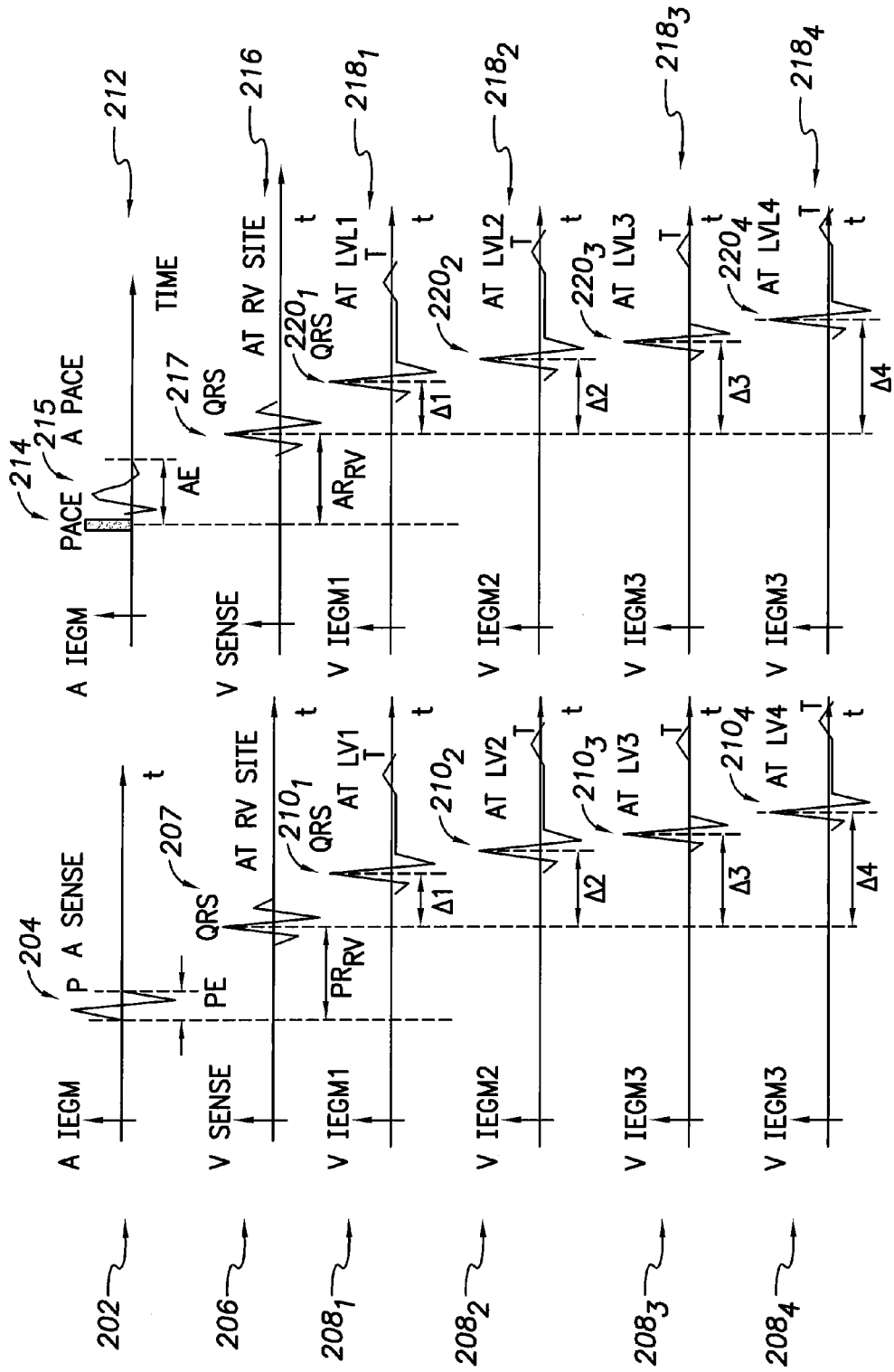
FIG. 4 is a graph illustrating an exemplary A-IEGM, RV-IEGM and set of LVn-IEGMs during V sense tests, and particularly illustrating $\Delta_n$ intervals exploited by the techniques of FIGS. 2-3.

More specifically, FIG. 4 illustrates, on its left-hand side, an A-IEGM 202 containing a P-wave 204. An RV IEGM 206 includes an RV QRS complex 207 triggered by the P-wave via AV conduction. A set of four LV IEGMs $208_1$-$208_4$ are shown. Each includes a version of a single LV QRS triggered by the P-wave via AV conduction, but sensed at slightly different times. The different versions of the LV QRS complex triggered by the P-wave are denoted $210_1$-$210_4$. FIG. 4 also illustrates, on its right-hand side, an A-IEGM 212 containing an A-pulse 214 and resulting atrial evoked response (ER) 215. (The ER may be detected to verify capture of the atrial pulse and, if necessary, the atrial pulse magnitude can be increased to compensate for any persistent lack of capture.) An RV IEGM 216 includes an RV QRS complex 217 triggered by the A-pulse via AV conduction. A set of four LV IEGMs $218_1$-$218_4$ are shown. Each includes a version of a single LV QRS triggered by the A-pulse via AV conduction, but sensed at slightly different times, denoted $220_1$-$220_4$. In FIG. 4, the T-wave associated with each QRS is identified by the letter "T".

Returning to FIG. 3, in response to detection of a P-wave on the A-IEGM, steps 222-226 are performed to measure or otherwise determine various intrinsic atrioventricular and interventricular intervals. In particular, at step 222, the pacer/ICD detects a $PR_{RV}$ interval between the P-wave of the A-IEGM and the RV-QRS of the RV-IEGM. At step 224, the device measures $\Delta_n$ between the RV QRS and each of the N LVn QRS complexes on the N LVn IEGM channels. Note that $\Delta_n$ values can be negative. If negative, the LV depolarizes first then the RV. If positive, the RV depolarizes first, then the LV.

At step 226, the device then determines $PR_{LVn}$ between the P-wave and each LVn QRS based on $PR_{RV}$ and the $\Delta_n$ values by, e.g., calculating $PR_{LVn}=PR_{RV}+\Delta_n$. Alternatively, the device could directly measure the time delays from the P-wave to each LVn QRS. In either case, a single P-wave can be used to ascertain values for $\Delta_n$ and $PR_{LVn}$ without needing to perform a separate V sense test for each separate LV electrode, thus saving time. Due to beat-to-beat variation, preferably a sufficient number of P-waves and resulting intervals are detected and measured to permit the device to calculate suitable average values. For example, a series of P-waves and resulting intervals may be detected and recorded over a predetermined period of time (such as over one minute) or for a predetermined number of heartbeats (such as at least eight beats.)

Examples of the various P-wave-triggered interval values determined during steps 222-226 are shown in FIG. 4. In these examples, the various intervals are measured between the start of the P-wave and the peaks of the resulting QRS complexes. Other points within these events could instead be used in other implementations to measure the intervals.

Within FIG. 3, in response to delivery of an A-pulse, steps 228-232 are performed to measure or otherwise determine various paced intervals. In particular, at step 228, the pacer/ICD detects an $AR_{RV}$ interval between the A-pulse and the RV-QRS of the RV-IEGM. At step 230, the device measures $\Delta_n$ between the RV QRS and each of the N LVn QRS complexes on the N LVn IEGM channels. At step 232, the device then determines $AR_{LVn}$ between the A-pulse and each LVn QRS based on $AR_{RV}$ and the $\Delta_n$ values by, e.g., calculating $AR_{LVn}=AR_{RV}+\Delta_n$. Alternatively, the device could directly measure the time delays from the A-pulse to each LVn QRS. In either case, a single A-pulse can be used to ascertain values for $\Delta_n$ and $AR_{LVn}$ without needing to perform a separate V sense test for each separate LV electrode, thus saving time. (As with P-waves, although a single A-pulse can be used to ascertain the various intervals, preferably a sufficient number of A-pulse and resulting intervals are detected and measured to permit the device to calculate suitable averages.)

Examples of the various A-pulse-triggered interval values determined during steps 228-232 are shown in FIG. 4. In these examples, the various intervals are measured between the A-pulse and the peaks of the resulting QRS complexes. Other points within these events could instead be used in other implementations to measure the intervals.

Continuing with FIG. 3, once intervals have been determined either from P-waves or from A-pulses, or both, then at step 234 the pacer/ICD performs a single multi-pole RV pace test to determine IVCD_RLn values for each of the N LV electrodes. This will be described more fully in connection with FIG. 5. At step 236, the device performs a set of N multi-pole LV pace tests to determine IVCD_LRn values for each of the N LV electrodes. This will also be described more fully in connection with FIG. 5. In some embodiments, the device also determines $IVCD\_L_1R$ and $IVCD\_L_nL_m$, values, which will be described more fully below with reference to FIGS. 11-14. At step 238, the device determines a set of N interventricular correction terms ($\epsilon_n$) from the IVCD_RLn and IVCD_LRn values using:

$$\epsilon_n = IVCD\_LRn - IVCD\_RLn.$$

At step 240, the pacer/ICD then selects one of the LV electrodes for biventricular pacing and sets the interventricular pacing delay ($VV_n$) for the selected electrode using:

$$VV_n = \alpha_n(\Delta_n + \epsilon_n)$$

where $\alpha_n$ is 0.5 or other predetermined coefficient. The device then delivers biventricular pacing using the RV electrode and the selected LV electrode using the determined VV delay. Alternatively, monoventricular pacing can be delivered by using the sign of $\Delta_n$ to determine the chamber to pace, i.e. either the RV or the LV.

As to the coefficient $\alpha_n$, $\alpha_n$ is a programmable or hard-coded parameter that may vary from patient to patient and from electrode to electrode. In some examples, each of the $\alpha_n$ values is set to 0.5, which is a default value. Otherwise routine testing may be employed to determine preferred or optimal values for $\alpha_n$ based, e.g., on an evaluation of the resulting hemodynamics within test patients. The values for $\alpha$ values may differ from electrode to electrode, i.e. $\alpha_1$ may be set to a different value than $\alpha_2$.

The choice of the particular LV electrode for use in pacing may be made based on various considerations. See, for example, the considerations set forth in U.S. patent application Ser. No. 11/416,922, of Min et al., filed May 2, 2006, entitled "System and Method for Determining Optimal Pacing Stimulation Sites Based on ECG Information." Within some patients, combinations of two or more LV electrodes may be used to deliver ventricular pacing pulses. See, for example, U.S. patent application Ser. No. 11/749,662, filed May 16, 2007, of Ryu et al., entitled "Adaptive Single Site and Multi-Site Ventricular Pacing." Also, special techniques may be used to perform V sense, RV pace and LV pace tests during atrial fibrillation (AF.) See, for example, U.S. patent application Ser. No. 12/507,679, of Min, filed Jul. 22, 2009, and entitled "Systems and Methods for Optimizing Ventricular Pacing Delays during Atrial Fibrillation." That particular document also describes template-matching techniques appropriate for use during AF or in any non-atrial tracking mode, such as VVI.

Where appropriate, the biventricular pacing of step 240 can be used in conjunction with other pacing therapy techniques, such as other CRT techniques. Briefly, CRT seeks to normalize asynchronous cardiac electrical activation and resultant asynchronous contractions associated with CHF by delivering synchronized pacing stimulus to both ventricles. The stimulus is synchronized so as to improve overall cardiac function. This may have the additional beneficial effect of reducing the susceptibility to life-threatening tachyarrhythmias.

Thus, FIG. 3 illustrates an exemplary technique for determining an optimal or preferred value for $VV_n$ for each of N LV electrodes. It should be understood that these values are not necessarily truly optimal in any particular quantifiable sense. As can be appreciated, what constitutes a truly "optimal" value depends on the criteria used for judging the resulting performance, which can be subjective in the minds of some clinicians. The values for $VV_n$ set at step 240 are, nevertheless, at least preferred values for use in pacing. Clinicians may choose to adjust these values via device programming for particular patients, at their discretion.

Figure 5:
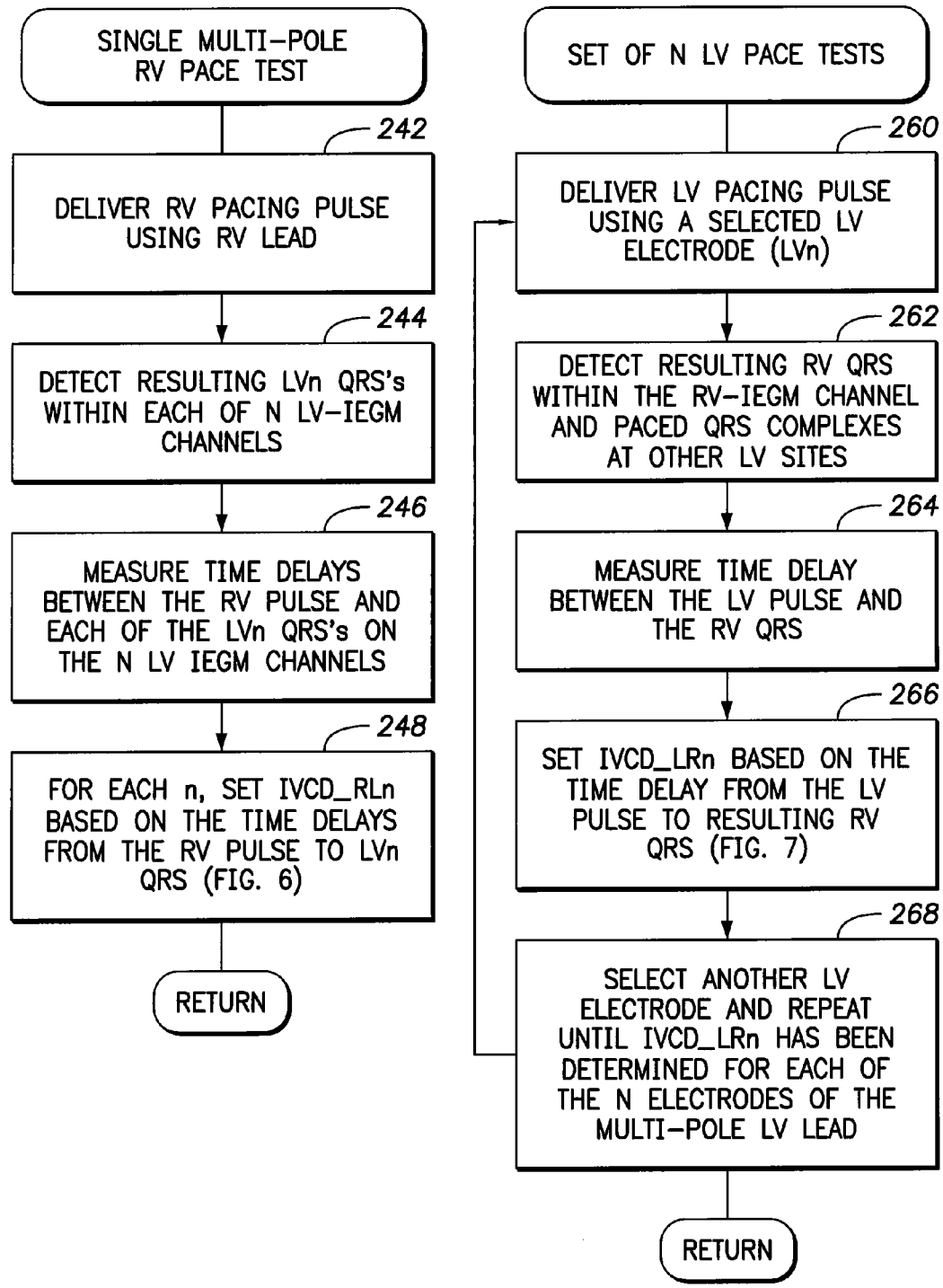
FIG. 5 is a flowchart exemplary techniques for performing RV pace and LV pace tests for use with the method of FIG. 3.
Figure 6:
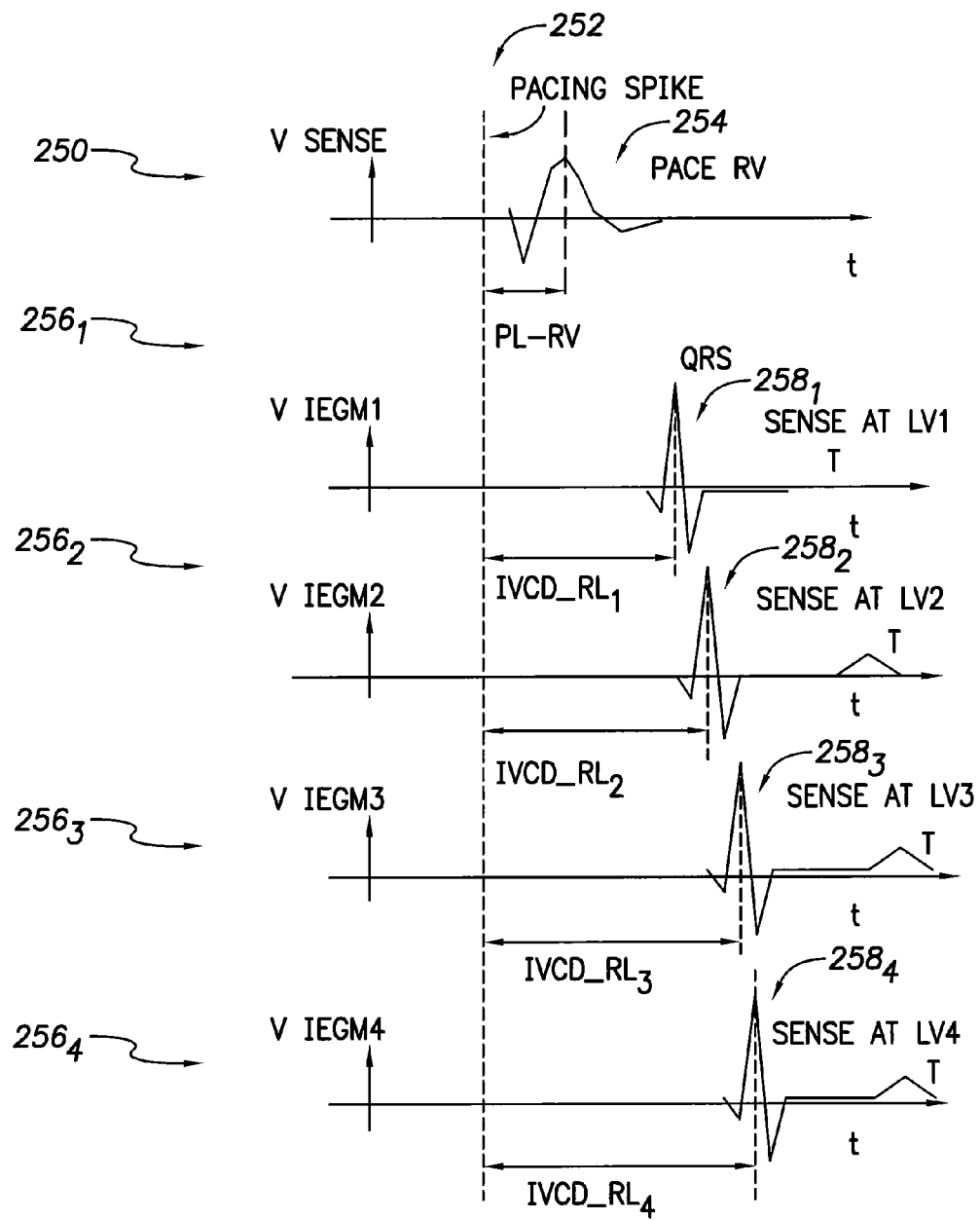
FIG. 6 is a graph illustrating an RV IEGM and a set of LVn IEGMs sensed during the RV pace test for use with the method FIG. 5.
Figure 7:
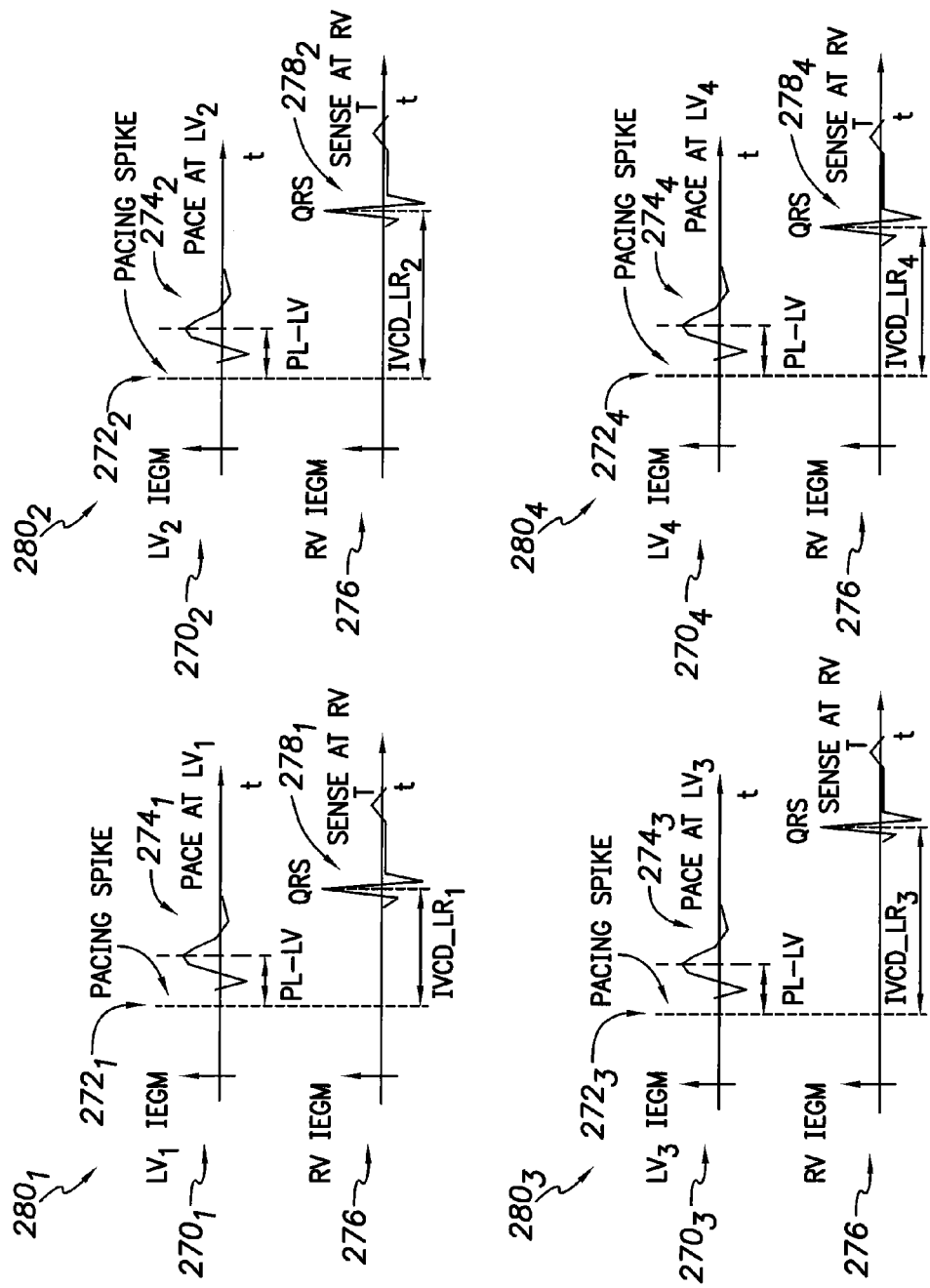
FIG. 7 includes several graphs illustrating various RV IEGMs and LVn IEGMs sensed during a set of LV pace tests for use with the method FIG. 5.

Turning now to FIGS. 5-7, techniques for performing RV and LV pace tests will be described. These tests determine values for IVCD_RLn and IVCD_LRn for use in determining the intrinsic interventricular correction term ($\epsilon_n$), which is used along with $\Delta_n$ to set $VV_n$ (as already explained.)

For an RV pace test, beginning at step 242 of FIG. 5, the pacer/ICD delivers an RV pacing pulse using the RV lead (which may include a tip/ring electrode pair for delivery of bipolar pulses to the RV). At step 244, the pacer/ICD detects resulting LVn QRS complexes on each of the N LVn channels. At step 246, the device then measure time delays between the RV pulse and each of the LV QRS complexes detected on the N LVn IEGM channels. At step 248, for each n, the device sets IVCD_RLn based on the time delays from the RV pulse to LVn QRS.

Exemplary RV and LVn IEGMs are shown in FIG. 6 (in stylized form) for a quadra-pole example of the RV pace test. More specifically, FIG. 6 illustrates an RV IEGM 250 that includes an RV evoked response 254 triggered by an RV-pulse 252. (The ER may be detected to verify capture of the RV pulse and, if necessary, the RV pulse magnitude can be increased to compensate for any persistent lack of capture.) A set of four LV IEGMs $256_1$-$256_4$ are shown. Each includes a version of a single LV QRS (or an LV "paced propagation") triggered by the RV-pulse via interventricular conduction, but sensed at slightly different times. The LV QRS complexes triggered by the RV-pulse are denoted $258_1$-$258_4$. The IVCD_RLn intervals are also shown.

Thus, a single RV-pulse can be used to ascertain values for IVCD_RLn without needing to perform a separate RV pace test for each separate LVn electrode, thus saving time. Although a single RV-pulse can be used to ascertain the IVCD_RLn intervals, preferably a sufficient number of RV-pulses and resulting IVCD_RLn intervals are detected and measured to permit the device to calculate suitable averages.

Returning to FIG. 5, similar steps are performed for an LV pace test, except that a set of N LV pace tests is performed, one test for each of the N LV electrodes. Briefly, beginning at step 260, the pacer/ICD delivers an LV pacing pulse using at least a selected one of the N LV electrodes of the LV lead. For example, an LV pulse may be delivered in a unipolar configuration between a selected LV electrode (such as "distal" or "tip" electrode $LV_1$) and the device housing. Alternatively, the pulse may be delivered in a bipolar configuration between any two adjacent LV electrodes, such as between $LV_1$ and $LV_2$, or between $LV_2$ and $LV_3$, or between $LV_3$ and $LV_4$ (i.e. the proximal LV lead.) These are just some examples. In general, bipolar pulses may be delivered LVn to LV(n−1) or LV(n+1). Still further, other combinations of LV electrodes can potentially be used to deliver pulses in the bipolar pulse configuration, such as $LV_1$ to $LV_4$, though adjacent electrode pairs are preferred. At step 262, the pacer/ICD detects a resulting RV QRS complex on the RV channels as well as paced QRS complexes at all other (non-paced) LV sites. At step 264, the device then measures the time delay between the LV pulse and the RV QRS complex (or RV paced propagation) detected on the RV IEGM channel. At step 266, the device sets IVCD_LRn based on the time delay from the LV pulse to RV QRS complex. At step 268, the pacer/ICD then selects another of the LVn electrodes and repeats steps 260-266 until a value for IVCD_LR has been determined for each of the N electrodes of the multi-pole LV lead.

Exemplary RV and LVn IEGMs are shown in FIG. 7 for a quadra-pole example of the LV pace test. More specifically, FIG. 7 illustrates a first LV pace test $280_1$ wherein an LV pulse $272_1$ is delivered via electrode $LV_1$, triggering an LV evoked response $274_1$ (which may be used to verify capture.) The LV evoked response is shown on an $LV_1$ IEGM sensed using the $LV_1$ electrode. The LV pulse also triggers an RV QRS (or RV paced propagation) $278_1$ via interventricular conduction, which is shown on an RV IEGM 276. The IVCD_LR interval between the LV pulse and the RV QRS is shown as $IVCD\_LR_1$. Preferably, a sufficient number of LV-pulses are delivered and resulting $IVCD\_RL_1$ intervals are measured to permit the device to calculate average values of $IVCD\_LR_1$ suitable for use in controlling VV pacing. It should be understood that, in some embodiments, in addition to detecting the RV QRS as shown, the pacer/ICD can also detect paced LV QRS complexes at each of the other (non-paced) LV sites and measures various interelectrode IVCD delays between the LV electrodes (e.g. $IVCD\_L_1L_2$). This is further shown by way of FIG. 14, discussed below. The various interelectrode IVCD delays (e.g. $IVCD\_L_nL_m$) can be exploited using techniques illustrated in FIGS. 11-12, also discussed below.

Similar tests are performed for the other LV electrodes. Briefly, a second LV pace test $280_2$ is shown wherein an LV pulse $272_2$ is delivered via electrode $LV_2$, triggering an LV evoked response $274_2$. The LV evoked response is shown on an $LV_2$ IEGM sensed using the $LV_2$ electrode. The LV pulse also triggers an RV QRS $278_2$ (which is shown on RV IEGM 276) and the IVCD interval $IVCD\_LR_2$ is measured. A third LV pace test $280_3$ is shown wherein an LV pulse $272_3$ is delivered via electrode $LV_3$, triggering an LV evoked response $274_3$. The LV evoked response is shown on an $LV_3$ IEGM sensed using the $LV_3$ electrode. The LV pulse also triggers an RV QRS $278_3$ (which is shown on RV IEGM 276) and the IVCD interval $IVCD\_LR_3$ is measured. A fourth LV pace test $280_4$ is shown wherein an LV pulse $272_4$ is delivered via electrode $LV_4$, triggering an LV evoked response $274_4$. The LV evoked response is shown on an $LV_4$ IEGM sensed using the $LV_4$ electrode. The LV pulse also triggers an RV QRS $278_4$ (which is shown on RV IEGM 276) and the IVCD interval $IVCD\_LR_4$ is measured. The various RV QRS events occur at slightly different times relative to the respective LV pulses and hence the values for IVCD_LR are all slightly different. In any case, these values are recorded and used in step 238 of FIG. 3 to determine values of $\epsilon_n$, which are used as explained above to set $VV_n$.

Although primarily described with respect to examples having a pacer/ICD, other implantable medical devices may be equipped to exploit the techniques described herein such as CRT devices and CRT-D devices. For the sake of completeness, an exemplary pacer/ICD will now be described, which includes components for performing the functions and steps already described.

Exemplary Pacer/ICD

Figure 8:
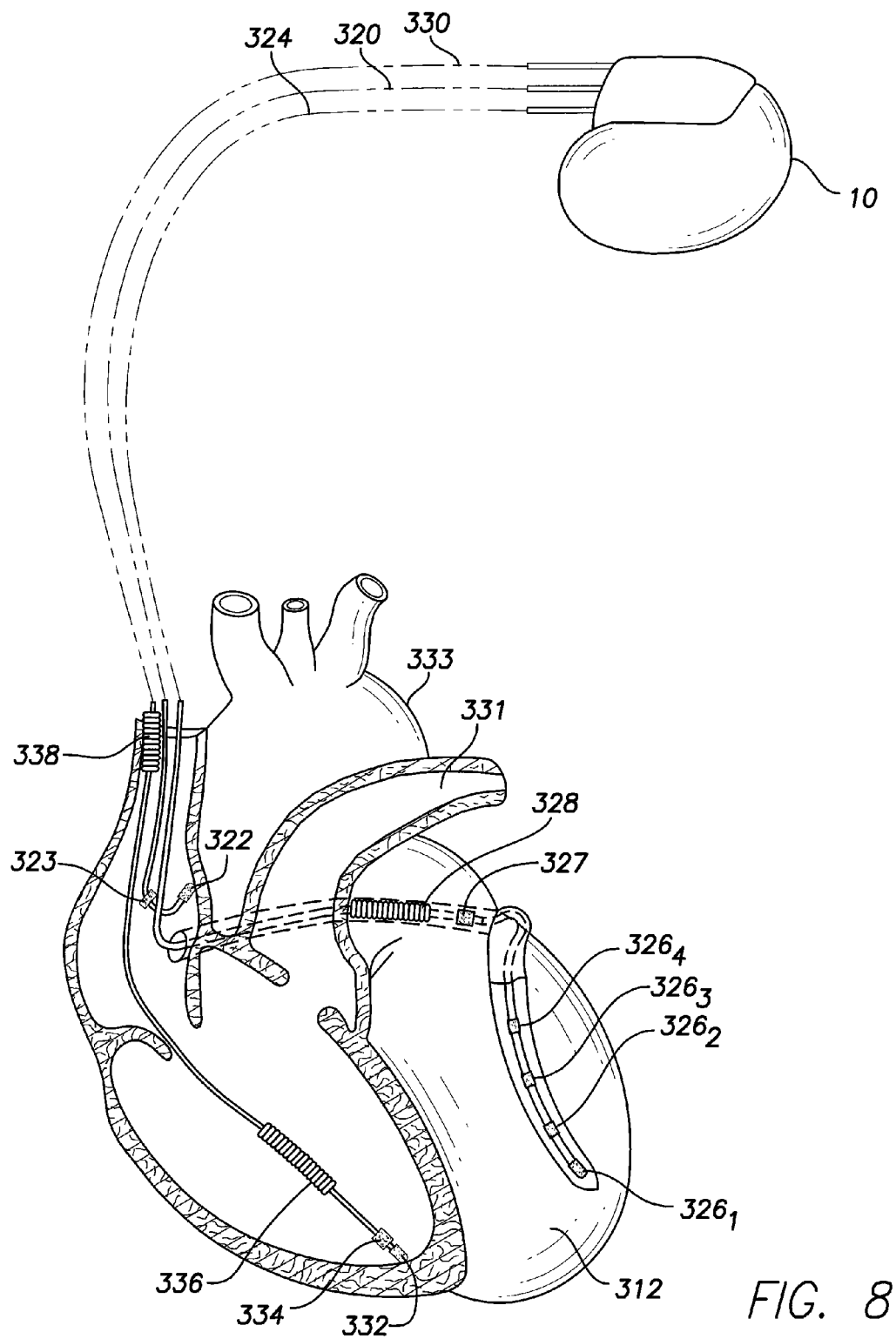
FIG. 8 is a simplified, partly cutaway view, illustrating the pacer/ICD of FIG. 1 along with at set of leads implanted into the heart of the patient.
Figure 9:
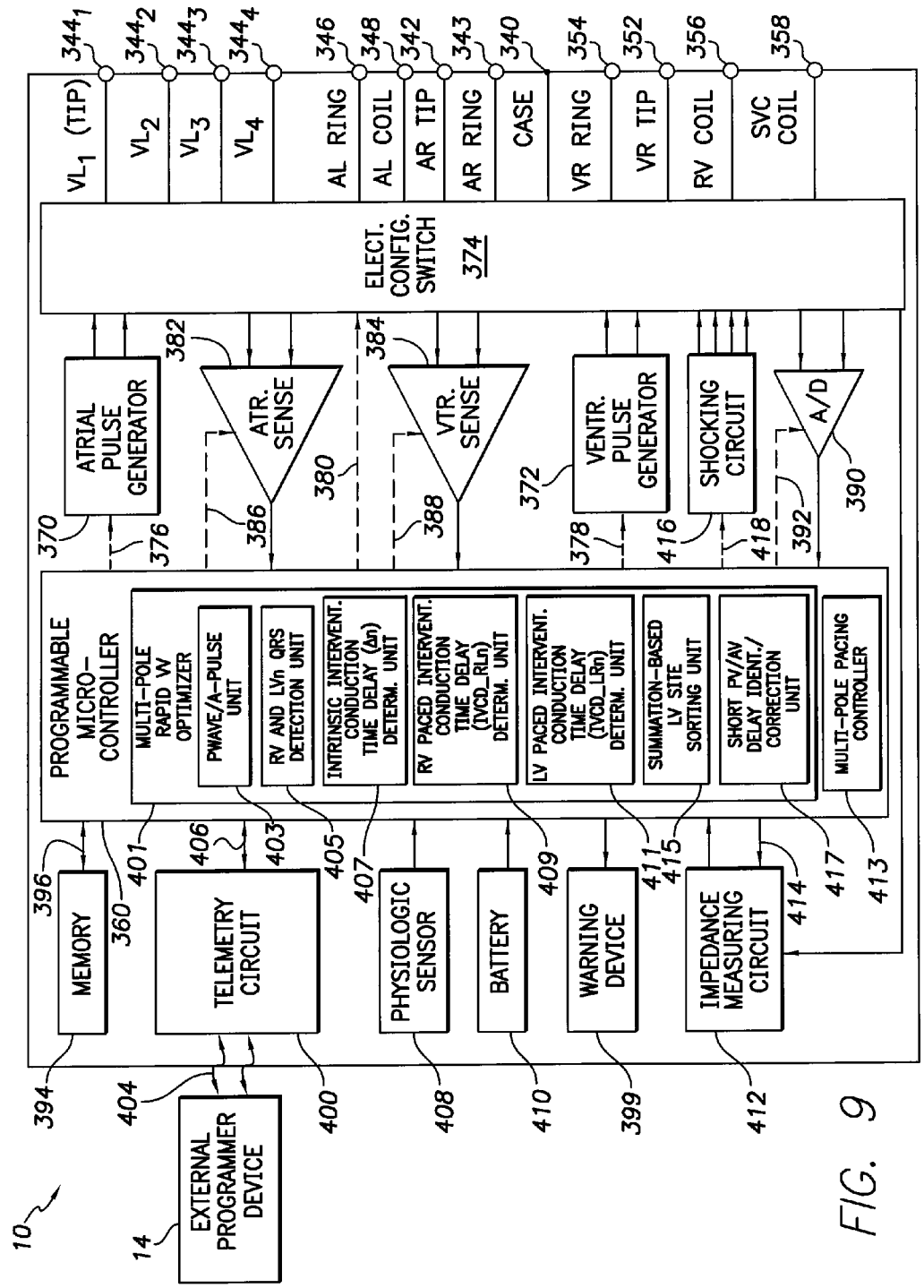
FIG. 9 is a functional block diagram of the pacer/ICD of FIG. 8, illustrating basic circuit elements that provide cardioversion, defibrillation and/or pacing stimulation in the heart an particularly illustrating an on-board optimization system for performing the optimization techniques of FIGS. 2-7.

With reference to FIGS. 8 and 9, a description of an exemplary pacer/ICD will now be provided. FIG. 5 provides a simplified block diagram of the pacer/ICD, which is a dual-chamber stimulation device capable of treating both fast and slow arrhythmias with stimulation therapy, including cardioversion, defibrillation, and pacing stimulation, and also capable of setting and using VV pacing delays, as discussed above. To provide other atrial chamber pacing stimulation and sensing, pacer/ICD 10 is shown in electrical communication with a heart 312 by way of a left atrial lead 320 having an atrial tip electrode 322 and an atrial ring electrode 323 implanted in the atrial appendage. Pacer/ICD 10 is also in electrical communication with the heart by way of a right ventricular lead 330 having, in this embodiment, a ventricular tip electrode 332, a right ventricular ring electrode 334, a right ventricular (RV) coil electrode 336, and a superior vena cava (SVC) coil electrode 338. Typically, the right ventricular lead 330 is transvenously inserted into the heart so as to place the RV coil electrode 336 in the right ventricular apex, and the SVC coil electrode 338 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a multi-pole LV lead 324 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary LV lead 324 is designed to receive atrial and ventricular cardiac signals and to deliver left ventricular pacing therapy using a set of four left ventricular electrodes $326_1$, $326_2$, $326_3$, and $326_4$ (thereby providing a quadra-pole lead), left atrial pacing therapy using at least a left atrial ring electrode 327, and shocking therapy using at least a left atrial coil electrode 328. The $326_1$ LV electrode may also be referred to as a "tip" or "distal" LV electrode. The $326_4$ LV electrode may also be referred to as a "proximal" LV electrode. In other examples, more or fewer LV electrodes are provided. Although only three leads are shown in FIG. 5, it should also be understood that additional leads (with one or more pacing, sensing and/or shocking electrodes) might be used and/or additional electrodes might be provided on the leads already shown, such as additional electrodes on the RV lead.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation. The housing 340 for pacer/ICD 10, shown schematically in FIG. 9, is often referred to as the "can", "case" or "case electrode" and may be programmably selected to act as the return electrode for all "unipolar" modes. The housing 340 may further be used as a return electrode alone or in combination with one or more of the coil electrodes, 328, 336 and 338, for shocking purposes. The housing 340 further includes a connector (not shown) having a plurality of terminals, 342, 343, $344_1$-$344_4$, 346, 348, 352, 354, 356 and 358 (shown schematically and, for convenience, the names of the electrodes to which they are connected are shown next to the terminals). As such, to achieve right atrial sensing and pacing, the connector includes at least a right atrial tip terminal ($A_R$ TIP) 342 adapted for connection to the atrial tip electrode 322 and a right atrial ring ($A_R$ RING) electrode 343 adapted for connection to right atrial ring electrode 323. To achieve left chamber sensing, pacing and shocking, the connector includes a left ventricular tip terminal ($VL_1$ TIP) $344_1$ and additional LV electrode terminals $344_2$-$344_4$ for the other LV electrodes of the quadra-pole LV lead.

The connector also includes a left atrial ring terminal ($A_L$ RING) 346 and a left atrial shocking terminal ($A_L$ COIL) 348, which are adapted for connection to the left atrial ring electrode 327 and the left atrial coil electrode 328, respectively. To support right chamber sensing, pacing and shocking, the connector further includes a right ventricular tip terminal ($V_R$ TIP) 352, a right ventricular ring terminal ($V_R$ RING) 354, a right ventricular shocking terminal ($V_R$ COIL) 356, and an SVC shocking terminal (SVC COIL) 358, which are adapted for connection to the right ventricular tip electrode 332, right ventricular ring electrode 334, the $V_R$ coil electrode 336, and the SVC coil electrode 338, respectively.

At the core of pacer/ICD 10 is a programmable microcontroller 360, which controls the various modes of stimulation therapy. As is well known in the art, the microcontroller 360 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 360 includes the ability to process or monitor input signals (data) as controlled by a program code stored in a designated block of memory. The details of the design and operation of the microcontroller 360 are not critical to the invention. Rather, any suitable microcontroller 360 may be used that carries out the functions described herein. The use of microprocessor-based control circuits for performing timing and data analysis functions are well known in the art.

As shown in FIG. 9, an atrial pulse generator 370 and a ventricular pulse generator 372 generate pacing stimulation pulses for delivery by the right atrial lead 320, the right ventricular lead 330, and/or the LV lead 324 via an electrode configuration switch 374. It is understood that in order to provide stimulation therapy in each of the four chambers of the heart, the atrial and ventricular pulse generators, 370 and 372, may include dedicated, independent pulse generators, multiplexed pulse generators or shared pulse generators. The pulse generators, 370 and 372, are controlled by the microcontroller 360 via appropriate control signals, 376 and 378, respectively, to trigger or inhibit the stimulation pulses.

The microcontroller 360 further includes timing control circuitry (not separately shown) used to control the timing of such stimulation pulses (e.g., pacing rate, AV delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 374 includes a plurality of switches for connecting the desired electrodes to the appropriate I/O circuits, thereby providing complete electrode programmability. Accordingly, the switch 374, in response to a control signal 380 from the microcontroller 360, determines the polarity of the stimulation pulses (e.g., unipolar, bipolar, combipolar, etc.) by selectively closing the appropriate combination of switches (not shown) as is known in the art. The switch also switches among the various LV electrodes.

Atrial sensing circuits 382 and ventricular sensing circuits 384 may also be selectively coupled to the right atrial lead 320, LV lead 324, and the right ventricular lead 330, through the switch 374 for detecting the presence of cardiac activity in each of the four chambers of the heart. Accordingly, the atrial (ATR. SENSE) and ventricular (VTR. SENSE) sensing circuits, 382 and 384, may include dedicated sense amplifiers, multiplexed amplifiers or shared amplifiers. The switch 374 determines the "sensing polarity" of the cardiac signal by selectively closing the appropriate switches, as is also known in the art. In this way, the clinician may program the sensing polarity independent of the stimulation polarity. Each sensing circuit, 382 and 384, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 382 and 384, are connected to the microcontroller 360 which, in turn, are able to trigger or inhibit the atrial and ventricular pulse generators, 370 and 372, respectively, in a demand fashion in response to the absence or presence of cardiac activity in the appropriate chambers of the heart.

For arrhythmia detection, pacer/ICD 10 utilizes the atrial and ventricular sensing circuits, 382 and 384, to sense cardiac signals to determine whether a rhythm is physiologic or pathologic. As used in this section "sensing" is reserved for the noting of an electrical signal, and "detection" is the processing of these sensed signals and noting the presence of an arrhythmia. The timing intervals between sensed events (e.g., AS, VS, and depolarization signals associated with fibrillation which are sometimes referred to as "F-waves" or "Fib-waves") are then classified by the microcontroller 360 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (ND) data acquisition system 390. The data acquisition system 390 is configured to acquire intracardiac electrogram signals, convert the raw analog data into a digital signal, and store the digital signals for later processing and/or telemetric transmission to an external device 402. The data acquisition system 390 is coupled to the right atrial lead 320, the LV lead 324, and the right ventricular lead 330 through the switch 374 to sample cardiac signals across any pair of desired electrodes. The microcontroller 360 is further coupled to a memory 394 by a suitable data/address bus 396, wherein the programmable operating parameters used by the microcontroller 360 are stored and modified, as required, in order to customize the operation of pacer/ICD 10 to suit the needs of a particular patient. Such operating parameters define, for example, the amplitude or magnitude, pulse duration, electrode polarity, for both pacing pulses and impedance detection pulses as well as pacing rate, sensitivity, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 394 through a telemetry circuit 400 in telemetric communication with the external device 402, such as a programmer, transtelephonic transceiver or a diagnostic system analyzer. The telemetry circuit 400 is activated by the microcontroller by a control signal 406. The telemetry circuit 400 advantageously allows intracardiac electrograms and status information relating to the operation of pacer/ICD 10 (as contained in the microcontroller 360 or memory 394) to be sent to the external device 402 through an established communication link 404. Pacer/ICD 10 further includes an accelerometer or other physiologic sensor 408, commonly referred to as a "rate-responsive" sensor because it is typically used to adjust pacing stimulation rate according to the exercise state of the patient. However, the physiological sensor 408 may further be used to detect changes in cardiac output, changes in the physiological condition of the heart, or diurnal changes in activity (e.g., detecting sleep and wake states) and to detect arousal from sleep. Accordingly, the microcontroller 360 responds by adjusting the various pacing parameters (such as rate, AV delay, VV delay, etc.) at which the atrial and ventricular pulse generators, 370 and 372, generate stimulation pulses. While shown as being included within pacer/ICD 10, it is to be understood that the physiologic sensor 408 may also be external to pacer/ICD 10, yet still be implanted within or carried by the patient. A common type of rate responsive sensor is an activity sensor incorporating an accelerometer or a piezoelectric crystal, which is mounted within the housing 340 of pacer/ICD 10. Other types of physiologic sensors are also known, for example, sensors that sense the oxygen content of blood, respiration rate and/or minute ventilation, pH of blood, ventricular gradient, etc.

The pacer/ICD additionally includes a battery 410, which provides operating power to all of the circuits shown in FIG. 9. The battery 410 may vary depending on the capabilities of pacer/ICD 10. If the system only provides low voltage therapy, a lithium iodine or lithium copper fluoride cell typically may be utilized. For pacer/ICD 10, which employs shocking therapy, the battery 410 should be capable of operating at low current drains for long periods, and then be capable of providing high-current pulses (for capacitor charging) when the patient requires a shock pulse. The battery 410 should also have a predictable discharge characteristic so that elective replacement time can be detected. Accordingly, appropriate batteries are employed.

As further shown in FIG. 9, pacer/ICD 10 is shown as having an impedance measuring circuit 412, which is enabled by the microcontroller 360 via a control signal 414. Uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 412 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 360 further controls a shocking circuit 416 by way of a control signal 418. The shocking circuit 416 generates shocking pulses of low (up to 0.5 joules), moderate (0.5-10 joules) or high energy (11 to 40 joules), as controlled by the microcontroller 360. Such shocking pulses are applied to the heart of the patient through at least two shocking electrodes, and as shown in this embodiment, selected from the left atrial coil electrode 328, the RV coil electrode 336, and/or the SVC coil electrode 338. The housing 340 may act as an active electrode in combination with the RV electrode 336, or as part of a split electrical vector using the SVC coil electrode 338 or the left atrial coil electrode 328 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 7-40 joules), delivered asynchronously (since R-waves may be too disorganized), and pertaining exclusively to the treatment of fibrillation. Accordingly, the microcontroller 360 is capable of controlling the synchronous or asynchronous delivery of the shocking pulses.

An internal warning device 399 may be provided for generating perceptible warning signals to the patient via vibration, voltage or other methods.

Insofar as ventricular pacing is concerned, the microcontroller includes a multi-pole rapid VV optimizer 401 operative to perform or control the techniques of FIGS. 2-7, described above. The optimizer includes a P-wave/A-pulse unit 403 operative to identify electrical events sufficient to trigger ventricular depolarization within the heart of the patient. A multi-pole LVn QRS detection unit 405 is operative to detect a resulting ventricular depolarization at each of a plurality of electrodes of the multi-pole LV lead. The RV QRS is detected by other components of the device.

A multi-pole intrinsic interventricular conduction time delay ($\Delta n$) determination unit 407 is operative to determine an interventricular conduction time delay for each of the electrodes of the multi-pole lead based on the depolarization triggered by A-pulses/P-waves, the conduction time delay including a paced interventricular conduction time delay and/or an intrinsic interventricular conduction time delay.

A multi-pole RV paced interventricular conduction time delay (IVCD_RLn) determination unit 409 controls RV pace tests to determine values for IVCD_RLn. A multi-pole LV paced interventricular conduction time delay (IVCD_LRn) determination unit 411 controls LV pace tests to determine values for IVCD_LRn. A multi-pole pacing controller 413 is operative to control ventricular pacing using a selected electrode of the multi-pole LV lead based on interventricular conduction time delays determined for that electrode during the V sense, RV pace and LV pace tests.

In addition to performing technique described above, the pacer/ICD of FIG. 9 can also perform the various techniques described below with reference to FIGS. 11-14. In particular, rapid optimizer 401 can perform of control the techniques of FIGS. 11-14. To this end, the rapid optimizer may include a summation-based LV site sorting unit 415 (operative to perform the techniques of FIG. 14, discussed below) and a short PV/AV delay identification and correction unit 417 (operative to perform the short PV/AV techniques of FIG. 12, also discussed below.)

Depending upon the implementation, the various components of the microcontroller may be implemented as separate software modules or the modules may be combined to permit a single module to perform multiple functions. In addition, although shown as being components of the microcontroller, some or all of these components may be implemented separately from the microcontroller, using application specific integrated circuits (ASICs) or the like.

As noted, at least some of the techniques described herein can be performed by (or under the control of) an external device. For the sake of completeness, an exemplary device programmer will now be described, which includes components for controlling at least some of the functions and steps already described.

Exemplary External Programmer

Figure 10:
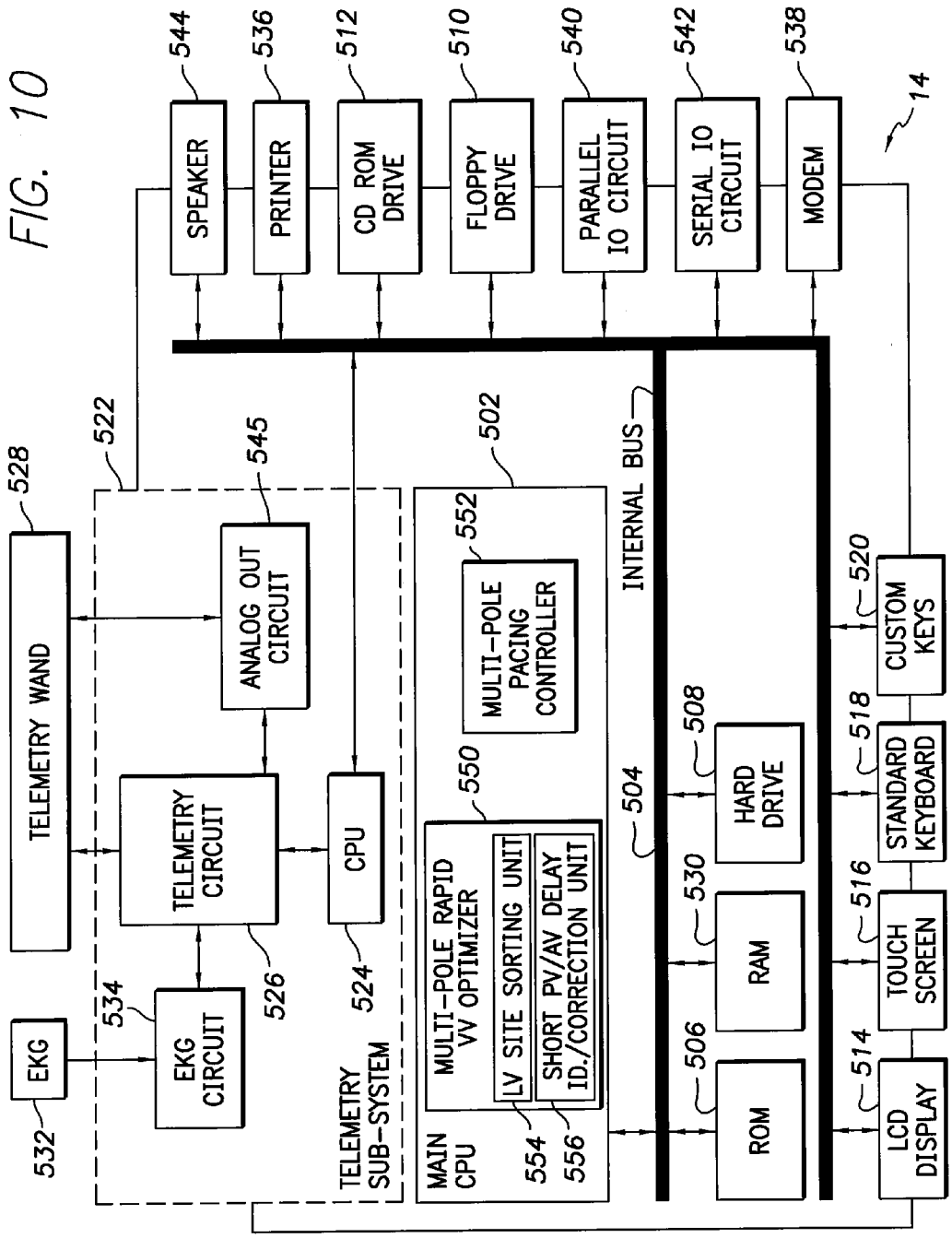
FIG. 10 is a functional block diagram illustrating components of the external device programmer of FIG. 1 and particularly illustrating programmer-based optimization systems for controlling the optimization techniques of FIGS. 2-7.

FIG. 10 illustrates pertinent components of an external programmer 14 for use in programming the pacer/ICD of FIG. 9 and for performing the above-described optimization techniques. For the sake of completeness, other device programming functions are also described herein. Generally, the programmer permits a physician or other user to program the operation of the implanted device and to retrieve and display information received from the implanted device such as IEGM data and device diagnostic data. Additionally, the external programmer can be optionally equipped to receive and display electrocardiogram (EKG) data from separate external EKG leads that may be attached to the patient. Depending upon the specific programming of the external programmer, programmer 14 may also be capable of processing and analyzing data received from the implanted device and from the EKG leads to, for example, render preliminary diagnosis as to medical conditions of the patient or to the operations of the implanted device.

Now, considering the components of programmer 14, operations of the programmer are controlled by a CPU 502, which may be a generally programmable microprocessor or microcontroller or may be a dedicated processing device such as an application specific integrated circuit (ASIC) or the like. Software instructions to be performed by the CPU are accessed via an internal bus 504 from a read only memory (ROM) 506 and random access memory 530. Additional software may be accessed from a hard drive 508, floppy drive 510, and CD ROM drive 512, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 514 or other suitable computer display device. To this end, the CPU may, for example, display a menu of specific programmable parameters of the implanted device to be programmed or may display a menu of types of diagnostic data to be retrieved and displayed. In response thereto, the physician enters various commands via either a touch screen 516 overlaid on the LCD display or through a standard keyboard 518 supplemented by additional custom keys 520, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various parameters are programmed. Typically, the physician initially controls the programmer 14 to retrieve data stored within any implanted devices and to also retrieve EKG data from EKG leads, if any, coupled to the patient. To this end, CPU 502 transmits appropriate signals to a telemetry subsystem 522, which provides components for directly interfacing with the implanted devices, and the EKG leads. Telemetry subsystem 522 includes its own separate CPU 524 for coordinating the operations of the telemetry subsystem. Main CPU 502 of programmer communicates with telemetry subsystem CPU 524 via internal bus 504. Telemetry subsystem additionally includes a telemetry circuit 526 connected to telemetry wand 528, which, in turn, receives and transmits signals electromagnetically from a telemetry unit of the implanted device. The telemetry wand is placed over the chest of the patient near the implanted device to permit reliable transmission of data between the telemetry wand and the implanted device. Herein, the telemetry subsystem is shown as also including an EKG circuit 534 for receiving surface EKG signals from a surface EKG system 532. In other implementations, the EKG circuit is not regarded as a portion of the telemetry subsystem but is regarded as a separate component.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the pacer/ICD also includes the data stored within the recalibration database of the pacer/ICD (assuming the pacer/ICD is equipped to store that data.) Data retrieved from the implanted devices is stored by external programmer 14 either within a random access memory (RAM) 530, hard drive 508 or within a floppy diskette placed within floppy drive 510. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 14, the implanted devices may be further controlled to transmit additional data in real time as it is detected by the implanted devices, such as additional IEGM data, lead impedance data, and the like. Additionally, or in the alternative, telemetry subsystem 522 receives EKG signals from EKG leads 532 via an EKG processing circuit 534. As with data retrieved from the implanted device itself, signals received from the EKG leads are stored within one or more of the storage devices of the external programmer. Typically, EKG leads output analog electrical signals representative of the EKG. Accordingly, EKG circuit 534 includes analog to digital conversion circuitry for converting the signals to digital data appropriate for further processing within the programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from optional external EKG leads. Data retrieved from the implanted devices includes parameters representative of the current programming state of the implanted devices. Under the control of the physician, the external programmer displays the current programmable parameters and permits the physician to reprogram the parameters. To this end, the physician enters appropriate commands via any of the aforementioned input devices and, under control of CPU 502, the programming commands are converted to specific programmable parameters for transmission to the implanted devices via telemetry wand 528 to thereby reprogram the implanted devices. Prior to reprogramming specific parameters, the physician may control the external programmer to display any or all of the data retrieved from the implanted devices or from the EKG leads, including displays of EKGs, IEGMs, and statistical patient information. Any or all of the information displayed by programmer may also be printed using a printer 536.

Additionally, CPU 502 also preferably includes an interval-based rapid VV optimizer 550 operative to perform or control the techniques of FIGS. 2-7, described above. CPU 502 also preferably includes a multi-pole rapid ventricular VV optimizer 550 and a multi-pole pacing controller operative to perform or control the techniques of FIGS. 2-7, described above. These components operate to analyze data received from the pacer/ICD, such as LVn-IEGM and RV-IEGM data, and to determine optimal or preferred $VV_n$ pacing delays for use in biventricular pacing or to determine the optimal ventricular chambers for use in monoventricular pacing. Pacing delay parameters and/or other pacing control information may then be transmitted to the pacer/ICD under the control the pacing controller to program the device to perform pacing in accordance with the optimal or preferred $VV_n$ pacing delays or in accordance with any monoventricular pacing control parameters.

In addition to performing technique described above, the system of FIG. 10 can also control or perform the various techniques described below with reference to FIGS. 11-14. In particular, rapid optimizer 550 can perform of control the techniques of FIGS. 11-14 based on data or other signals received from a pacer/ICD. To this end, the rapid optimizer may include a summation-based LV site sorting unit 554 (operative to control or perform the techniques of FIG. 14, discussed below) and a short PV/AV delay identification and correction unit 556 (operative to perform the short PV/AV techniques of FIG. 12, also discussed below.)

Programmer/monitor 14 also includes a modem 538 to permit direct transmission of data to other programmers via the public switched telephone network (PSTN) or other interconnection line, such as a T1 line or fiber optic cable. Depending upon the implementation, the modem may be connected directly to internal bus 504 may be connected to the internal bus via either a parallel port 540 or a serial port 542. Other peripheral devices may be connected to the external programmer via parallel port 540 or a serial port 542 as well. Although one of each is shown, a plurality of input output (IO) ports might be provided. A speaker 544 is included for providing audible tones to the user, such as a warning beep in the event improper input is provided by the physician. Telemetry subsystem 522 additionally includes an analog output circuit 545 for controlling the transmission of analog output signals, such as IEGM signals output to an EKG machine or chart recorder.

With the programmer configured as shown, a physician or other user operating the external programmer is capable of retrieving, processing and displaying a wide range of information received from the implanted device and to reprogram the implanted device if needed. The descriptions provided herein with respect to FIG. 10 are intended merely to provide an overview of the operation of programmer and are not intended to describe in detail every feature of the hardware and software of the programmer and is not intended to provide an exhaustive list of the functions performed by the programmer.

In the following additional and/or alternative techniques are described wherein the order by which LV sites are paced is sorted and optimized and wherein circumstances where AV/PV pacing delays are longer than corresponding AR/PR conduction delays are addressed.

Additional Multi-Pole LV Pacing Optimization Techniques

Figure 11:
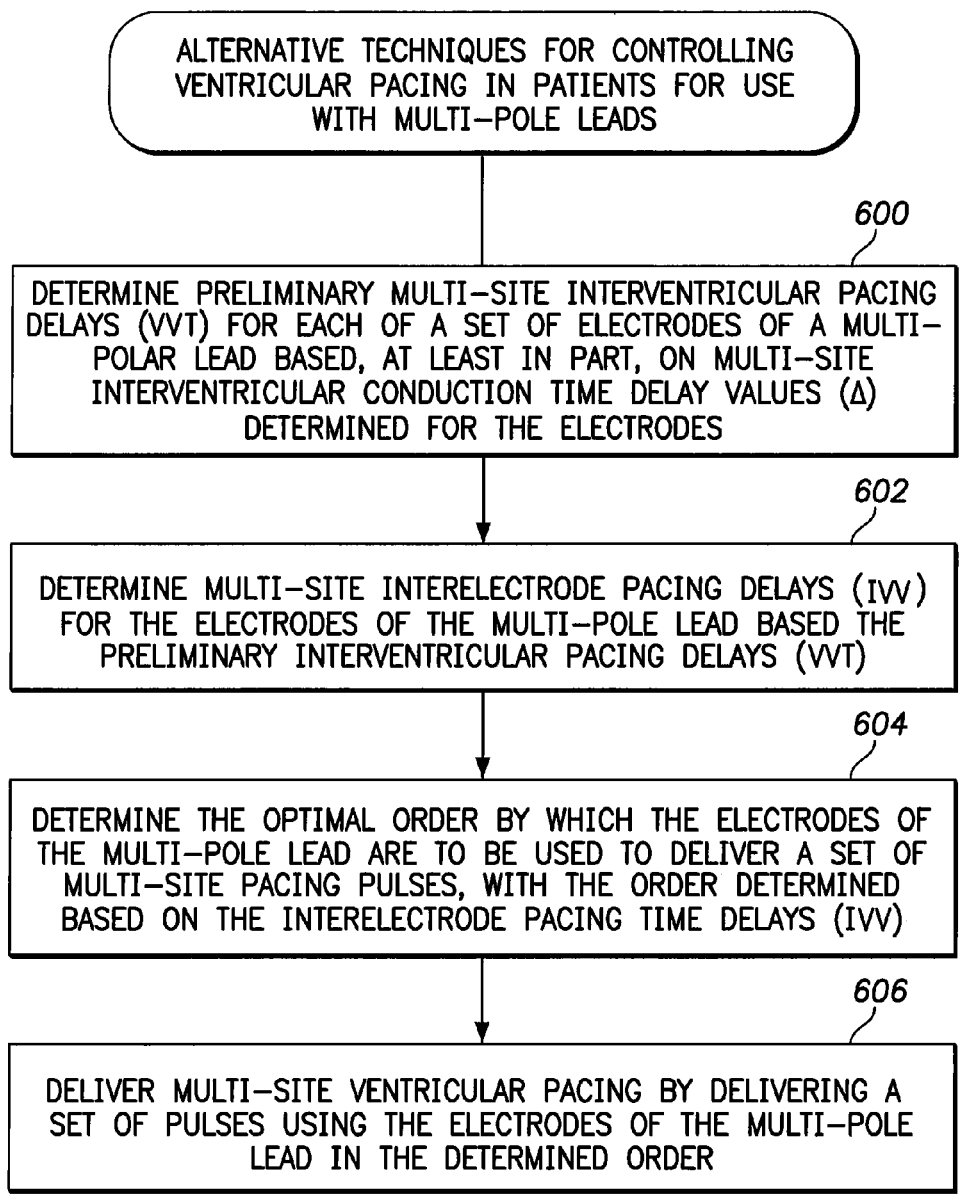
FIG. 11 is a flowchart providing an overview of an alternative technique for controlling ventricular pacing using a multi-pole LV lead, which may be performed by the system of FIG. 1 wherein steps are taken to determine the order by which a set of multi-site pacing pulses are to be delivered to various sites within the ventricles.

FIG. 11 broadly summarizes an alternative technique for controlling ventricular pacing for use with a multi-pole ventricular lead that may be exploited by the pacer/ICD of FIG. 1 or other suitably equipped systems. Beginning at step 600, the pacer/ICD determines preliminary multi-site interventricular pacing time delays (VVT) for each of a set of electrodes of a multi-polar lead based on multi-site interventricular conduction time delay values ($\Delta$) determined for the electrodes. At step 602, the device determines multi-site interelectrode pacing delays (IVV) for the electrodes of the multi-pole lead based the preliminary interventricular pacing delays (VVT). In one example described below, the IVV values are derived from the preliminary VVT values using a particular summation technique that iteratively sums the various interelectrode delays. At step 604, the device determines the preferred or optimal order by which the electrodes of the multi-pole lead are to be used to deliver multi-site pacing pulses, with the order determined based on the interelectrode pacing time delays (IVV) using techniques to be described below. For the example of MSLV pacing, the pacer/ICD determines the order by which a set of MSLV pulses are to be delivered using the electrodes of the multi-pole LV lead. At step 606, the device then delivers multi-site ventricular pacing by delivering (or controlling the delivery of) a set of pulses using the electrodes of the multi-pole lead in the order determined at step 604. As will be explained, the pulses are delivered subject to a set of final interventricular pacing delays (W), which are derived from IVV values. Note that these multi-site stimulation pulses are typically delivered in the sorted sequence during a single cardiac cycle. These techniques will be described in more detail with reference to the remaining figures.

Figure 12:
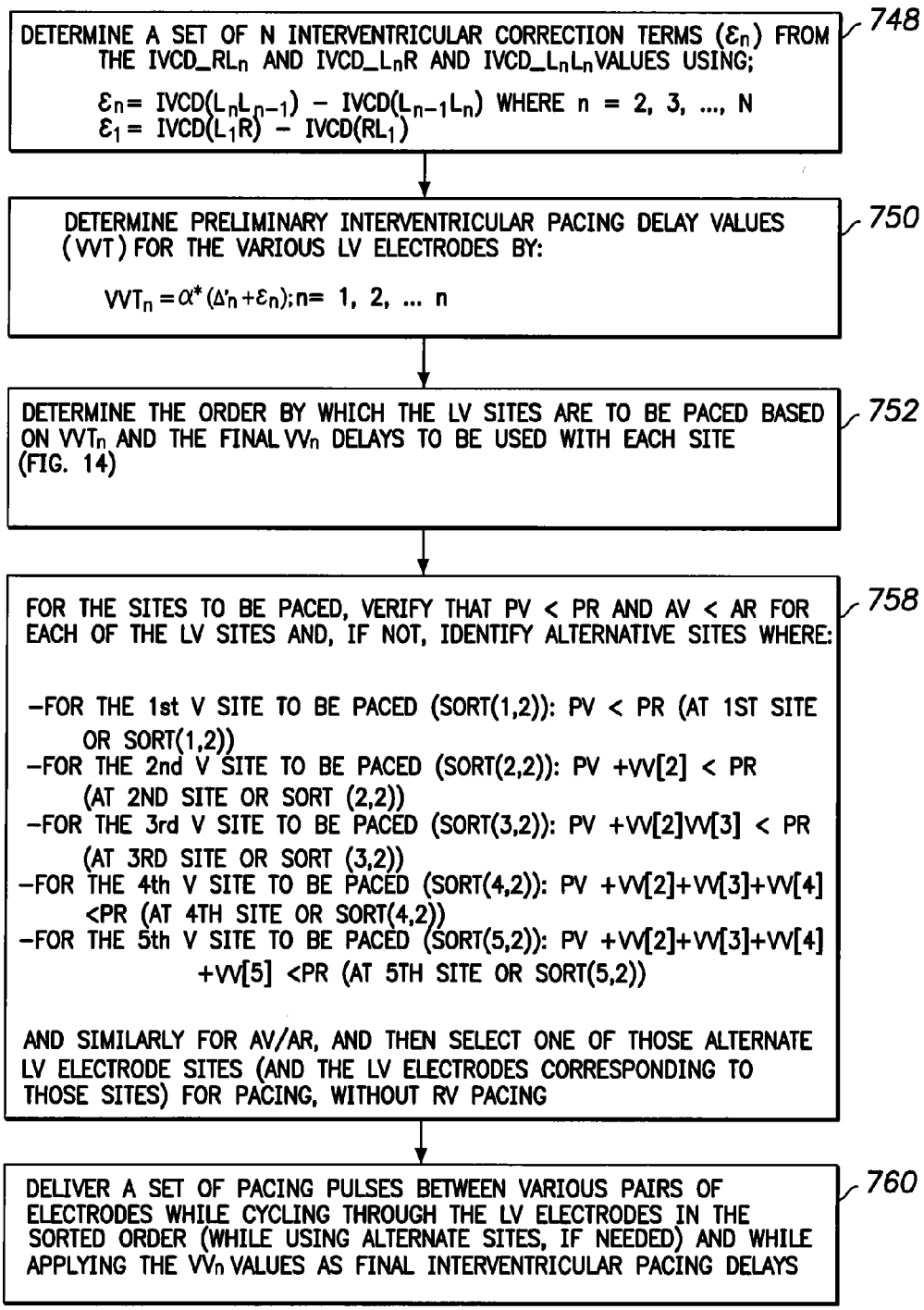
FIG. 12 is a flowchart illustrating an exemplary biventricular implementation of the technique of FIG. 11 wherein V sense, RV pace and LV pace tests are used to determine optimal interventricular pacing delays and wherein circumstances are addressed where PV pacing delays to be used are longer than intrinsic PR delays or where AV pacing delays to be used are longer than intrinsic AR delays.

FIG. 12 provides a more detailed example wherein MSLV pacing is controlled for use with a multi-pole LV lead having N electrodes (individually denoted $LV_n$ where n=0 ... N−1). Note that some of the initial steps of FIG. 12 are the same or similar to those of FIG. 3, discussed above and will not be described again in detail. Beginning at step 700, the pacer/ICD performs a single V sense test. As explained above, during the V sense test, the pacer/ICD: detects P-waves on an A-IEGM channel sensed using an RA lead and/or delivers A-pulse to the RA using the RA lead. Also at step 700, the pacer/ICD senses RV-IEGM and N individual $LV_n$-IEGM signals along N sensing vectors between the RV tip electrode and each of the respective $LV_n$ electrodes. The device also detects $LV_n$-QRS events within the $LV_n$-IEGMs and detects RV-QRS events within the RV-IEGM. Exemplary RV and $LV_n$ IEGMs are shown in FIG. 4, discussed above.

In response to detection of a P-wave on the A-IEGM, steps 722-726 are performed to measure or otherwise determine various intrinsic atrioventricular and interventricular intervals. In particular, at step 722, the pacer/ICD detects a $PR_{RV}$ interval between the P-wave of the A-IEGM and the RV-QRS of the RV-IEGM. At step 724, the device measures intrinsic interventricular conduction delays ($\Delta_n$) between the RV QRS and each corresponding $LV_n$ QRS complex on the N $LV_n$ IEGM channels. Note that $\Delta_n$ values can be negative. If negative, the LV depolarizes first then the RV. If positive, the RV depolarizes first, then the LV.

At step 725, the device determines interelectrode delays ($\Delta'_n$) from the interventricular conduction delays ($\Delta_n$) based on:

$$\Delta'_n = \Delta_n - \Delta_{n-1}; \text{ where } n=2, 3, \ldots, N$$

$$\Delta'_1 = \Delta_1$$

wherein $\Delta_n$ is the measured intrinsic interventricular conduction time delay for the nth electrode of the multi-pole lead.

At step 726, the device then determines $PR_{LVn}$ between the P-wave and each $LV_n$ QRS based on $PR_{RV}$ and the $\Delta_n$ values by, e.g., calculating $PR_{LVn}=PR_{RV}+\Delta_n$. Note that a single P-wave can be used to ascertain values for $\Delta_n$ and $PR_{LVn}$ without needing to perform a separate V sense test for each separate LV electrode, thus saving time.

Examples of the various P-wave-triggered interval values determined during steps 722-726 are also shown in FIG. 4. In the examples, the various intervals are measured between the start of the P-wave and the peaks of the resulting QRS complexes. Other points within these events could instead be used in other implementations to measure the intervals.

Within FIG. 12, in response to delivery of an A-pulse, steps 728-732 are performed to measure or otherwise determine various paced intervals. In particular, at step 728, the pacer/ICD detects an $AR_{RV}$ interval between the A-pulse and the RV-QRS of the RV-IEGM. At step 730, the device measures $\Delta_n$ between the RV QRS and each of the N LVn QRS complexes on the N LVn IEGM channels.

At step 731, the device determines interelectrode delays ($\Delta'_n$) values based on:

$$\Delta'_n = \Delta_n - \Delta_{n-1}; \text{ where } n=2, 3, \ldots, N$$

$$\Delta'_1 = \Delta_1$$

wherein $\Delta_n$ is again the measured intrinsic interventricular conduction time delay for the nth electrode of the multi-pole lead.

At step 732, the device then determines $AR_{LVn}$ between the A-pulse and each LVn QRS based on $AR_{RV}$ and the $\Delta_n$ values by, e.g., calculating $AR_{LVn}=AR_{RV}+\Delta_n$. A single A-pulse can be used to ascertain values for $\Delta_n$ and $AR_{LVn}$ without needing to perform a separate V sense test for each separate LV electrode, thus saving time.

Examples of various A-pulse-triggered interval values measured during steps 728-732 are shown in FIG. 4. In these examples, the various intervals are measured between the A-pulse and the peaks of the resulting QRS complexes. Other points within these events could instead be used in other implementations to measure the intervals.

Continuing with FIG. 12, once intervals have been determined either from P-waves or from A-pulses, or both, then at step 734 the pacer/ICD performs a single multi-pole RV pace test to determine IVCD_RL$_n$ values for each of the N LV electrodes. This was described more fully above in connection with FIG. 5. At step 736, the device performs a set of N multi-pole LV pace tests to determine IVCD_LRn values for each of the N LV electrodes. This was described in connection with FIG. 5. See, also, FIG. 13, which more clearly shows that, for each of the LV pace tests, the pacer/ICD measures an entire set of interelectrode delays.

Figure 13:
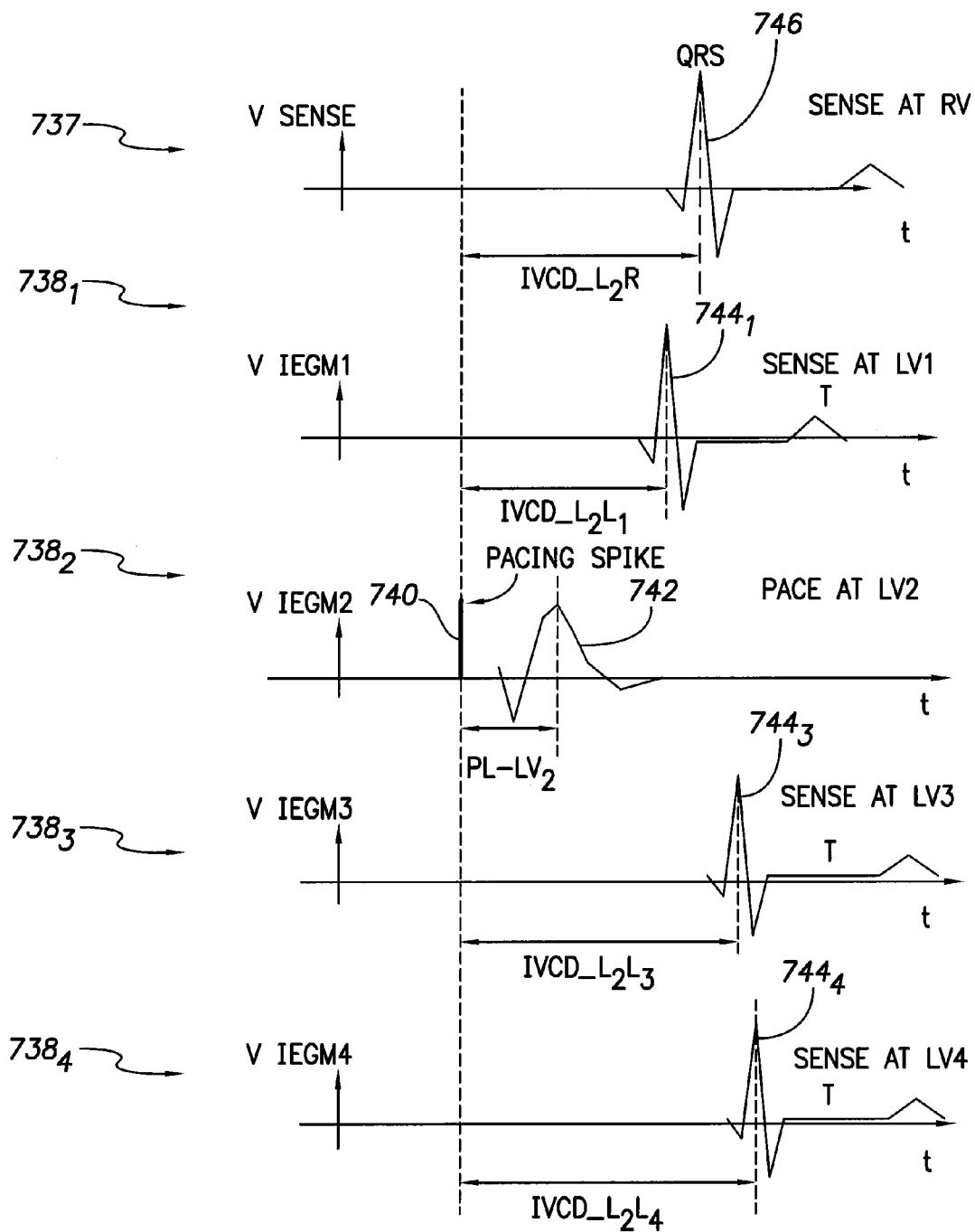
FIG. 13 is a graph illustrating exemplary $LV_n$-IEGMs during one of a set of four LV pace tests exploited during the technique of FIG. 12.

In FIG. 13, a first graph 737 illustrates an V sense IEGM sensed using the RV electrode (in a unipolar configuration, i.e. RV tip-to-can). A set of graphs 738$_1$-738$_4$ illustrate IEGMs sensed using the various LV electrodes (again in unipolar configuration.) In this particular example, a pacing pulse or spike 740 is applied using the second LV electrode, trigger an evoked response 742 at the site of the second LV electrode and a set of paced QRS complexes 744$_1$, 744$_3$, and 744$_4$ at the other LV sites (as well as a paced QRS 746 in the RV.) Various IVCD values are measured from the time of the pacing pulse at the various paced QRS complexes, including IVCD_L$_2$R, IVCD_L$_2$L$_1$, IVCD_L$_2$L$_3$, and IVCD_L$_2$L$_4$, as shown.

Additionally, for the quadra-pole example, three other LV pace tests are performed by delivering LV pulses to the other LV electrodes. For example, an LV pulse is delivered using the LV$_1$ electrode so as to trigger paced QRS's at the other LV sites to allow measurement of corresponding IVCD values between the LV$_1$ electrode and the other sites (IVCD_L$_1$R, IVCD_L$_1$L$_2$, IVCD_L$_1$L$_3$, and IVCD_L$_1$L$_4$.) Likewise, pulses are delivered at LV$_3$ and LV$_4$ to detect still other IVCD values.

Returning to FIG. 12, at step 748, the device determines a set of N interventricular correction terms ($\epsilon_n$) from the IVCD values using:

$$\epsilon_n = \text{IVCD}(L_n L_{n-1}) - \text{IVCD}(L_{n-1} L_n) \text{ where } n=2, 3, \ldots, N$$

$$\epsilon_1 = \text{IVCD}(L_1 R) - \text{IVCD}(R L_1)$$

wherein IVCD represents the paced interventricular conduction time delay (IVCD) for various pairs of electrodes of the system as determined using RV pace and LV pace tests and N is the number of electrodes.

At step 750, the pacer/ICD then selects a set of LV electrodes for MSLV pacing and sets the interventricular pacing delays (VVT$_n$) for the electrodes using:

$$VVT_n = \alpha_n(\Delta'_n + \epsilon_n); n=1, 2, \ldots, N$$

where $\alpha_n$ is 0.5 or other predetermined coefficient. As noted above, $\alpha_n$ is a programmable or hard-coded parameter that may vary from patient to patient and from electrode to electrode. The vales for $\alpha_n$ for use with step 750 of FIG. 12 may differ from those used in connection with the techniques discussed above. At step 752, the pacer/ICD then determines the order by which the LV sites are to be paced during MSLV pacing based on VVT$_n$. One technique for determining the order of MSLV pacing is shown in FIG. 14.

Figure 14:
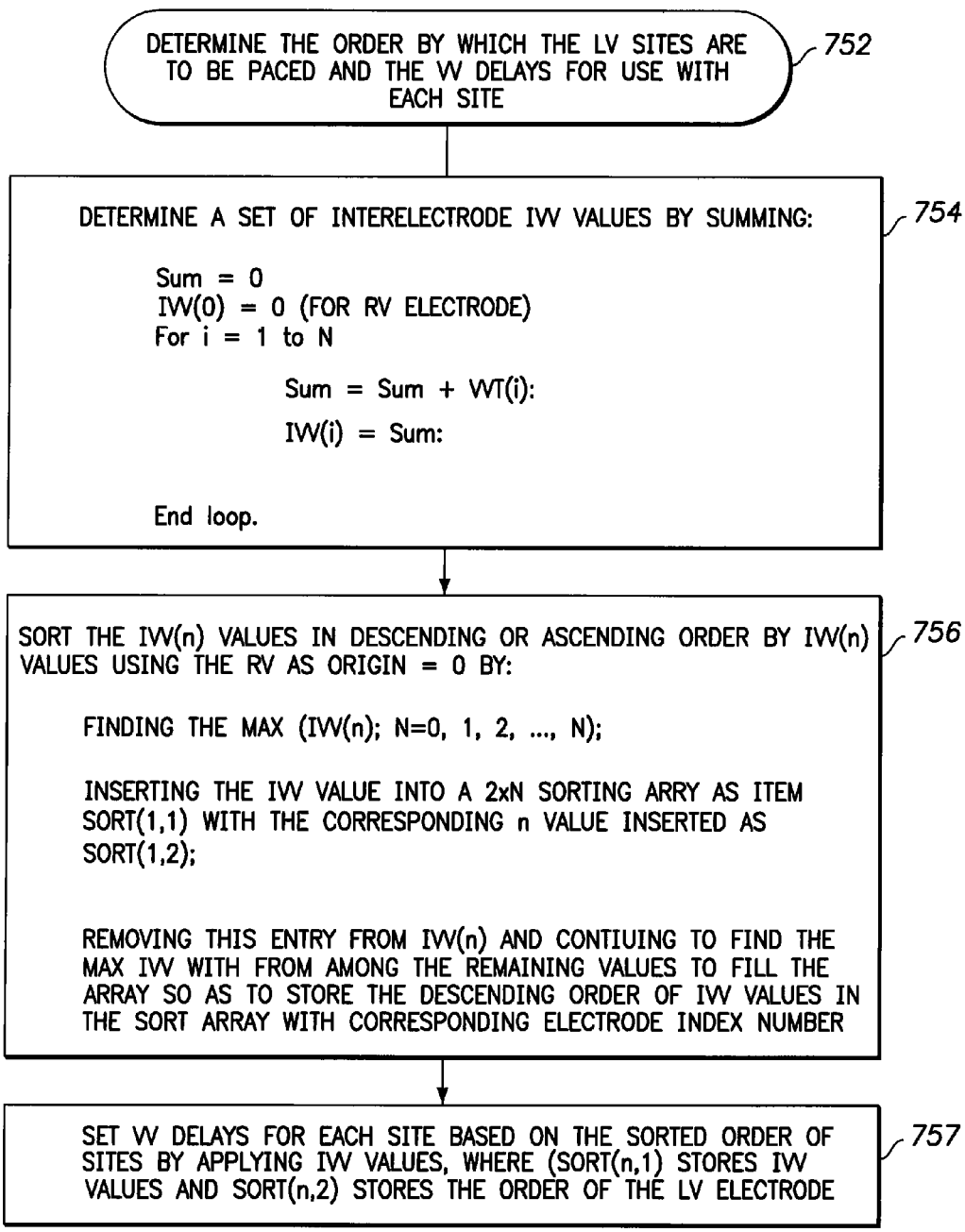
FIG. 14 is a flowchart illustrating a method for use with the technique of FIG. 12 for determining the order by which LV sites are to be paced and for determining $VV_n$ values.

At step 754 of FIG. 14, the pacer/ICD determine a set of interelectrode VV (IVV) values by summing:

```
Sum=0
IVV(0)=0 (for RV electrode)
For i=1 to N
    Sum=Sum+VVT(i);
    IVV(i)=Sum;
End loop.
```

As such, for the quadra-pole example:

$$IVV(1) = VVT(1)$$

$$IVV(2) = VVT(1) + VVT(2)$$

$$IVV(3) = VVT(1) + VVT(2) + VVT(2)$$

$$IVV(4) = VVT(1) + VVT(2) + VVT(3) + VVT(4).$$

Then, at step 756, the pacer/ICD sorts the IVV(n) values in descending or ascending order by IVV(n) values using the RV as the origin (i.e. 0) by:

finding the max (IVV(n); i=0, 1, 2, ..., N);
inserting the IVV value into a 2×N sorting array as item sort(1,1) with the corresponding n value inserted as sort(1,2)
removing this entry from IVV(n) and continuing to find the max IVV with from among the remaining values to fill the array so as to store the descending order of IVV values in the sort array with corresponding electrode index number. [Note that, if min is instead used in sorting instead of max, ascending order is generated instead of descending order.]

Then, at step 757, the device sets the VV delays for each site based on the sorted order of sites by applying IVV values as follows (where sort(n,1) stores IVV values and sort(n,2) stores the order of LV electrode):

the 1st V site to be paced is sort(1,2) with AV delay as determined and VV[1]=0;
the 2nd V site to be paced is sort(2,2) with VV[2] delay of (sort(1,1)−sort(2,1))
the 3rd V site to be paced is sort(3,2) with VV[3] delay of (sort(2,1)−sort(3,1))
the 4th V site to be paced is sort(4,2) with VV[4] delay of (sort(3,1)−sort(4,1)); and
the 5th V site to be paced is sort(5,2) with VV[5] delay of (sort(4,1)−sort(5,1))

and where:

$$VV[1] = 0;$$

$$VV[2] = (\text{sort}(1,1) - \text{sort}(2,1))$$

$$VV[3] = (\text{sort}(2,1) - \text{sort}(3,1))$$

$$VV[4] = (\text{sort}(3,1) - \text{sort}(4,1))$$

$$VV[5] = (\text{sort}(4,1) - \text{sort}(5,1)).$$

Thus, using this technique, the device finds the max of absolute (IVV$_n$)=max (IVV). The site with max IVV is the site to be paced first with the PV and AV delays from the formula set forth below. IVV is sorted in descending (or, alternatively, in ascending order) by IVV(n) values with RV as origin (i.e. RV=0.) In one particular example, the order with which stimulation pulses are to be delivered to the four electrodes of the LV lead is: 3rd electrode, 1st electrode, 2nd electrode and 4th electrode, with the RV electrode paced last. That is, the sorted order is: IVV(3), IVV(1), IVV(2), IVV(4), RV=0. In that example, the VV delay applied at the 3rd electrode (VV$_3$) is IVV(3); the VV delay applied at the 1st electrode (VV$_1$) is: IVV(3)-IVV(1); the VV delay applied at the 2nd electrode (VV$_2$) electrode is: IVV(1)-IVV(2); the VV delay applied at the 4th electrode ($VV_4$) electrode is IVV(2)-IVV(4); and the delay applied to the RV electrode is IVV(4)-0.

Returning to FIG. 12, at step 758 the device then determines if the VVT values result in PV and AV values that are sufficiently short. That is, for the LV sites to be paced, the device verifies that PV<PR and AV<AR for each of the LV sites and, if not, the device identify alternative sites where:
for PR/PV:
    for the 1st V site to be paced (sort(1,2)): PV<PR (at $1^{st}$ site or sort(1,2))
    for the 2nd V site to be paced (sort(2,2)): PV+VV[2]<PR (at $2^{nd}$ site or sort(2,2))
    for the 3rd V site to be paced (sort(3,2)): PV+VV[2] VV[3]<PR (at $3^{rd}$ site or sort(3,2))
    for the 4th V site to be paced (sort(4,2)): PV+VV[2]+VV[3]+VV[4]<PR (at $4^{th}$ site or sort(4,2))
    for the 5th V site to be paced (sort(5,2)): PV+VV[2]+VV[3]+VV[4]+VV[5]<PR (at $5^{th}$ site or sort(5,2)) and
for AR/AV:
    for the 1st V site to be paced (sort(1,2)): AV<AR (at $1^{st}$ site or sort(1,2))
    for the 2nd V site to be paced (sort(2,2)): AV+VV[2]<AR (at $2^{nd}$ site or sort(2,2))
    for the 3rd V site to be paced (sort(3,2)): AV+VV[2] VV[3]<AR (at $3^{rd}$ site or sort(3,2))
    for the 4th V site to be paced (sort(4,2)): AV+VV[2]+VV[3]+VV[4]<AR (at $4^{th}$ site or sort(4,2))
    for the 5th V site to be paced (sort(5,2)): AV+VV[2]+VV[3]+VV[4]+VV[5]<AR (at $5^{th}$ site or sort(5,2))
and then select one of those alternate LV electrode sites. The device then selects one of those alternate LV electrode sites (and the LV electrodes corresponding to those sites) for pacing. These alternative sites are to be paced without RV pacing. That is, all MSLV pacing will be LV only, with no pacing delivered using the RV.

At step 760, the device then delivers a set of MSLV pacing pulses between the selected pairs of electrodes while cycling through the LV electrodes corresponding to the selected sites in the sorted order (as determined at step 752) and while applying the $VV_n$ values as final interventricular pacing delay (as determined at step 757 of FIG. 14) and while also using alternate sites, if needed, as indicated at step 758. Where appropriate, the MSLV pacing of step 760 can be used in conjunction with other pacing therapy techniques, such as other CRT techniques.

Thus, FIG. 12 illustrates exemplary techniques for determining optimal or preferred values for $VV_n$ for a set of N LV electrodes for use in MSLV pacing. It should again be understood that these values are not necessarily truly optimal in any particular quantifiable sense. As can be appreciated, what constitutes a truly optimal value depends on the criteria used for judging the resulting performance, which can be subjective in the minds of some clinicians. The values for $VV_n$ used at step 760 are, nevertheless, at least preferred values for use in pacing. Clinicians may choose to adjust these values via device programming for particular patients, at their discretion.

In general, while the invention has been described with reference to particular embodiments, modifications can be made thereto without departing from the scope of the invention. Note also that the term "including" as used herein is intended to be inclusive, i.e. "including but not limited to."

What is claimed is:

1. A method for controlling multi-site ventricular pacing for use by an implantable cardiac rhythm management device equipped with a multi-pole ventricular lead having a plurality of electrodes, the method comprising:
    determining an interventricular conduction time delay value ($\Delta$) for each of the plurality of electrodes of the multi-pole lead;
    determining preliminary multi-site interventricular pacing delays (VVT) for the plurality of electrodes of the multi-pole lead based, at least in part, on the multi-site interventricular conduction time delay values ($\Delta$) determined for the electrodes;
    determining multi-site interelectrode pacing delays (IVV) for the plurality of electrodes of the multi-pole lead based on the preliminary interventricular pacing delays (VVT);
    determining an order by which the electrodes of the multi-pole lead are to be used to deliver a set of multi-site pacing pulses, with the order determined based on the interelectrode pacing time delays (IVV); and
    delivering multi-site ventricular pacing by delivering a set of pulses using the electrodes of the multi-pole lead in the determined order.

2. The method of claim 1 wherein the multi-pole lead is a left ventricular (LV) lead having a plurality of electrodes ($LV_n$) and the device is equipped with a right ventricular (RV) lead and wherein the method is performed to deliver multi-site LV (MSLV) pacing using the plurality of electrodes ($LV_n$) of the multi-pole LV lead, where n=1, 2 . . . , N.

3. The method of claim 2 wherein determining the preliminary interventricular pacing delays (VVT) includes setting an individual preliminary interventricular pacing delay ($VVT_n$) for use with a selected electrode ($LV_n$) of the LV lead based on:

$$VVT_n = \alpha_n (\Delta'_n + \epsilon_n);$$

wherein $\alpha_n$ is a coefficient, $\Delta'_n$ is an intrinsic interelectrode conduction time delay, $\epsilon_n$ is an interventricular correction term for use with the selected electrode ($LV_n$) of the LV lead and N represents the total number of electrodes of the multi-pole lead.

4. The method of claim 3 wherein determining the intrinsic interelectrode conduction time delays ($\Delta'_n$) comprises using:

$$\Delta'_n = \Delta_n - \Delta_{n-1}; \text{ where } n = 2, 3, \ldots, N$$

$$\Delta'_1 = \Delta_1$$

wherein $\Delta_n$ is a measured intrinsic interventricular conduction time delay for the nth electrode of the multi-pole lead.

5. The method of claim 4 wherein determining the interventricular correction term ($\epsilon_n$) comprises using:

$$\epsilon_n = IVCD(L_n L_{n-1}) - IVCD(L_{n-1} L_n) \text{ where } n = 2, 3, \ldots, N$$

$$\epsilon_1 = IVCD(L_1 R) - IVCD(RL_1)$$

wherein each value of IVCD represents a paced interventricular conduction time delay (IVCD).

6. The method of claim 3 wherein determining multi-site interelectrode pacing delays (IVV) for the plurality of electrodes based the preliminary interventricular pacing delays (VVT) includes:
    setting an individual interelectrode pacing delay ($IVV_n$) for use with a selected electrode ($LV_n$); and
    sequentially summing values of $VVT_n$ to generate corresponding values for $IVV_n$.

7. The method of claim 6 wherein determining an order by which the electrodes of the multi-pole lead are to be used to deliver a set of multi-site pacing pulses:

determining absolute values of each of the $IVV_n$ values;

identifying a particular $IVV_n$ value having a maximum absolute value and then selecting the corresponding electrode as being a first electrode to be used for delivering MSLV pacing; and repeating the process with the remaining $IVV_n$ values and the remaining electrodes to iteratively sort the $IVV_n$ values and the corresponding electrodes.

8. The method of claim 7 wherein delivering multi-site ventricular pacing includes:

determining final interventricular pacing delays ($VV_n$) for use with each of the electrodes of the LV lead based on differences between $IVV_n$ values of the electrodes;

delivering a first MSLV pulse using the first selected electrode; and delivering additional MSLV pulses using the other electrodes of the multi-pole lead in the sorted order and subject to the final interventricular pacing delays $VV_n$.

9. The method of claim 8 further including a predecessor step of determining multi-site interventricular conduction time delay values ($\Delta$) for the electrodes of the LV lead by:

identifying an electrical event sufficient to trigger ventricular depolarization within a heart of a patient in which the device is implanted;

detecting a resulting ventricular depolarization at each of a plurality of electrodes of the LV lead, the depolarization being detected at generally different times at each different electrode; and determining multi-site interventricular conduction time delays ($\Delta_n$) for each of the plurality of electrodes of the LV lead based on the depolarization triggered by the electrical event.

10. The method of claim 9 wherein detecting the resulting ventricular depolarization at each of a plurality of electrodes of the LV lead includes detecting a resulting LV QRS complex ($LV_n$ QRS) at each of the plurality of LV electrodes ($LV_n$) of the LV lead.

11. The method of claim 1 wherein the implantable medical device performs the determining steps.

12. The method of claim 1 wherein the implantable medical device transmits signals to an external device and the external device performs at least some of the determining steps.

13. A system for controlling ventricular pacing for use by an implantable cardiac rhythm management device equipped with a multi-pole ventricular lead having a plurality of electrodes, the system comprising:

an interventricular conduction time delay determination unit operative to determine a mulit-site interventricular conduction time delay value ($\Delta$) for each of the plurality of electrodes;

a multi-site interventricular pacing delay determination unit operative to determine preliminary multi-site interventricular pacing delays (VVT) for the plurality of electrodes of the multi-pole lead based, at least in part, on the multi-site interventricular conduction time delay values ($\Delta$) determined for the electrodes;

a multi-site interelectrode pacing delay determination unit operative to determine multi-site interelectrode pacing delays (IVV) for the plurality of electrodes of the multi-pole lead based on the preliminary interventricular pacing delays (VVT);

a multi-pole pacing site ordering unit operative to determine an order by which the electrodes of the multi-pole lead are to be used to deliver a set of multi-site pacing pulses, with the order determined based on the interelectrode pacing time delays (IVV); and a multi-pole ventricular pacing controller operative to deliver a set of pulses using the electrodes of the multi-pole lead.

14. A system for controlling ventricular pacing for use by an implantable cardiac rhythm management device equipped with a multi-pole ventricular lead having a plurality of electrodes, the system comprising:

means for determining a multi-site interventricular conduction time delay value ($\Delta$) for each of the plurality of electrodes;

means for determining preliminary multi-site interventricular pacing delays (VVT) for the plurality of electrodes of the multi-pole lead based, at least in part, on multi-site interventricular conduction time delay values ($\Delta$) determined for the electrodes;

means for determining multi-site interelectrode pacing delays (IVV) for the plurality of electrodes of the multi-pole lead based on the preliminary interventricular pacing delays (VVT);

means for determining an order by which the electrodes of the multi-pole lead are to be used to deliver a set of multi-site pacing pulses, with the order determined based on the interelectrode pacing time delays (IVV); and means for delivering multi-site ventricular pacing by delivering a set of pulses using the electrodes of the multi-pole lead.

* * * * *